(12) United States Patent
Ferrara-Cook et al.

(10) Patent No.: US 12,280,046 B2
(45) Date of Patent: Apr. 22, 2025

(54) MELANOCORTIN SUBTYPE-2 RECEPTOR (MC2R) ANTAGONIST FOR THE TREATMENT OF DISEASE

(71) Applicant: Crinetics Pharmaceuticals, Inc., San Diego, CA (US)

(72) Inventors: Christine Ferrara-Cook, San Diego, CA (US); Alan S. Krasner, San Diego, CA (US)

(73) Assignee: CRINETICS PHARMACEUTICALS, INC., San Diego, CA (US)

( * ) Notice: Subject to any disclaimer, the term of this patent is extended or adjusted under 35 U.S.C. 154(b) by 61 days.

(21) Appl. No.: 17/696,279

(22) Filed: Mar. 16, 2022

(65) Prior Publication Data

US 2022/0313691 A1  Oct. 6, 2022

Related U.S. Application Data

(60) Provisional application No. 63/298,571, filed on Jan. 11, 2022, provisional application No. 63/163,310, filed on Mar. 19, 2021.

(51) Int. Cl.
  *A61K 31/496* (2006.01)
  *A61K 9/00* (2006.01)
  *A61K 31/573* (2006.01)
  *A61P 5/08* (2006.01)

(52) U.S. Cl.
  CPC .......... *A61K 31/496* (2013.01); *A61K 9/0053* (2013.01); *A61K 31/573* (2013.01); *A61P 5/08* (2018.01)

(58) Field of Classification Search
  CPC .................................................. A61K 31/496
  See application file for complete search history.

(56) References Cited

U.S. PATENT DOCUMENTS

| | | | |
|---|---|---|---|
| 5,284,956 A | 2/1994 | Buchecker et al. | |
| 7,960,341 B2 | 6/2011 | Hathaway et al. | |
| 10,562,884 B2 | 2/2020 | Han et al. | |
| 10,604,507 B2 | 3/2020 | Han et al. | |
| 10,766,877 B2 | 9/2020 | Han et al. | |
| 10,981,894 B2 | 4/2021 | Han et al. | |
| 2003/0158209 A1 | 8/2003 | Dyck et al. | |
| 2004/0053933 A1 | 3/2004 | Pontillo et al. | |
| 2004/0192676 A1 | 9/2004 | Chen et al. | |
| 2005/0119252 A1 | 6/2005 | Tucci et al. | |
| 2005/0192286 A1 | 9/2005 | Tran et al. | |
| 2010/0222339 A1 | 9/2010 | Chen et al. | |
| 2010/0305122 A1 | 12/2010 | Bruncko et al. | |
| 2013/0184285 A1 | 7/2013 | Brain et al. | |
| 2019/0367481 A1* | 12/2019 | Han ..................... | C07D 407/14 |
| 2020/0010452 A1 | 1/2020 | Han et al. | |
| 2020/0172611 A1 | 6/2020 | Feldhaus et al. | |
| 2020/0216415 A1 | 7/2020 | Han et al. | |
| 2021/0238164 A1 | 8/2021 | Han et al. | |
| 2022/0023266 A1 | 1/2022 | Farber et al. | |
| 2023/0015914 A1 | 1/2023 | Han et al. | |

FOREIGN PATENT DOCUMENTS

| | | |
|---|---|---|
| EP | 1403251 A1 | 3/2004 |
| EP | 2448582 B1 | 4/2017 |
| EP | 3199156 A1 | 8/2017 |
| EP | 3480198 A1 | 5/2019 |
| KR | 20130116002 A | 10/2013 |
| WO | WO-9964002 A1 | 12/1999 |
| WO | WO-0074679 A1 | 12/2000 |
| WO | WO-03009847 A1 | 2/2003 |
| WO | WO-03009850 A1 | 2/2003 |
| WO | WO-03031410 A1 | 4/2003 |
| WO | WO-03045918 A1 | 6/2003 |
| WO | WO-03068738 A1 | 8/2003 |
| WO | WO-03094918 A1 | 11/2003 |
| WO | WO-2004058735 A2 | 7/2004 |
| WO | WO-2004083209 A1 | 9/2004 |
| WO | WO-2005014563 A1 | 2/2005 |
| WO | WO-2005023260 A1 | 3/2005 |
| WO | WO-2005040109 A1 | 5/2005 |
| WO | WO-2005040136 A1 | 5/2005 |
| WO | WO-2005042516 A2 | 5/2005 |
| WO | WO-2006113704 A2 | 10/2006 |
| WO | WO-2007047496 A2 | 4/2007 |
| WO | WO-2007133108 A1 | 11/2007 |
| WO | WO-2010026124 A1 | 3/2010 |
| WO | WO-2012163354 A1 | 12/2012 |
| WO | WO-2019014460 A1 | 1/2019 |
| WO | WO-2019079373 A1 | 4/2019 |
| WO | WO-2019236699 A1 | 12/2019 |
| WO | WO-2021091788 A1 | 5/2021 |
| WO | WO-2021126693 A1 | 6/2021 |

(Continued)

OTHER PUBLICATIONS

Non-Classic Congenital Adrenal Hyperplasia: What Do Endocrinologists Need to Know? Jha et al. Endocrinol Metab Clin North Am. Mar. 2021; 50(1): 151-165. (Year: 2021).*
Effects of Chronic ACTH Excess on Human Adrenal Cortex Bertagna et al. Front. Endocrinol. 8:43 (Year: 2017).*
Fukuoka et al. The Mechanisms Underlying Autonomous Adrenocorticotropic Hormone Secretion in Cushing's Disease. Int J Mol Sci. 21(23):9132 (2020).
PCT/US2022/020543 International Search Report and Written Opinion dated Jul. 26, 2022.
PCT/US2022/020543 Invitation to Pay Additional Fees dated May 24, 2022.

(Continued)

*Primary Examiner* — Jeffrey S Lundgren
*Assistant Examiner* — Eric Tran
(74) *Attorney, Agent, or Firm* — WILSON SONSINI GOODRICH & ROSATI

(57) ABSTRACT

Provided herein are methods and compositions for the treatment of diseases of ACTH excess, such as Cushing's disease, ectopic ACTH syndrome, and congenital adrenal hyperplasia.

18 Claims, 15 Drawing Sheets

(56) References Cited

FOREIGN PATENT DOCUMENTS

| WO | WO-2021133563 A1 | 7/2021 |
|---|---|---|
| WO | WO-2022036123 A1 | 2/2022 |
| WO | WO-2022197798 A1 | 9/2022 |
| WO | WO-2023163945 A1 | 8/2023 |
| WO | WO-2024130091 A1 | 6/2024 |

OTHER PUBLICATIONS

Angelousi et al. ACTH action on the adrenals. [Updated Oct. 26, 2016]. In: Feingold KR, Anawalt B, Boyce A, et al., editors. Endotext [Internet]. South Dartmouth (MA): MDText.com, Inc .; 2000-. Available from: https://www.ncbi.nlm.nih.gov/books/NBK279118/.
Arasasingham et al. Structure-activity relationship of (1-aryl-2-piperazinylethyl)piperazines: antagonists for the AGRP/melanocortin receptor binding. J Med Chem 46:9-11 (2003).
Berge et al. Pharmaceutical Salts. Journal of Pharmaceutical Sciences 66(1):1-19 (Jan. 1977).
Chen et al. Identification and characterization of pyrrolidine diastereoisomers as potent functional agonists and antagonists of the human melanocortin-4 receptor. Bioorg Med Chem Lett 18:129-136 (2008).
Chen et al. Pharmacological and pharmacokinetic characterization of 2-piperazine-a-isopropyl benzylamine derivatives as melanocortin-4 receptor antagonists. Bioorg Med Chem 16:5606-5618 (2008).
Ciato et al. Currently used and investigational drugs for Cushing's disease. Expert Opin Investig Drugs 26(1):75-84 (2016).
Clark et al. ACTH antagonists. Front. Endocrinol. 7:101 (2016a).
Creemers et al. Cushing's syndrome: an update on current pharmacotherapy and future directions. Expert Opin Pharmacother 16(12):1829-1844 (2015).
Gantz et al. The melanocortin system. Am. J. Physiol. Endocrinol. Metab. 284:E468-E474 (2003).
Kusnetzow et al. Discovery and Identification of Late Stage, Selective Nonpeptide ACTH Antagonists for the Treatment of Cushing's Disease, Ectopic ACTH Secreting Tumors, and Congenital Adrenal Hyperplasia. Poster # MON-176. ENDO Online 2020. Jun. 8-22, 2020.
Kusnetzow et al. Nonpeptide, Orally Bioavailable ACTH Antagonists: suppression of ACTH-induced Corticosterone Secretion and Adrenal Hypertrophy in Rats. Poster # SAT-364. ENDO 2019. Mar. 23-26, 2019; New Orleans.
Lacroix et al. Cushing's syndrome. Lancet 386(9996):913-927 (2015).
Malik et al. Adrenocorticotropic hormone (ACTH) responses require actions of the melanocortin-2 receptor accessory protein on the extracellular surface of the plasma membrane. J Biol Chem 290(46):27972-27985 (2015).
Markison et al. Effects of Nonpeptide Orally Bioavailable ACTH Antagonists on Adrenal Gland Size and Function in Rats. Crinetics Pharmaceuticals PowerPoint Presentation e-ECE 2020.
Newfield. ACTH receptor blockade: a novel approach to treat congenital adrenal hyperplasia, or Cushing's disease. Med Hypotheses 74(4):705-706 (2010).
Nieman et al. Treatment of Cushing's Syndrome: An Endocrine Society Clinical Practice Guideline. J Clin Endocrinol Metab 100(8):2807-2831 (2015).
Nieman. Overview of the treatment of Cushing's syndrome. In: UpToDate (Oct. 30, 2019), Topic 174 Version 15.0. Waltham, MA: UpToDate Inc. https://www.uptodate.com/contents/overview-of-the-treatment-of-cushings-syndrome?csi=fd4b2565-633a-424b-becb-a44daecca8aa&source=contentShare. (Accessed May 20, 2020).
Nieman. Recent updates on the diagnosis and management of Cushing's syndrome. Endocrinol Metab (Seoul) 33(2):139-146 (2018).
Ramachandrappa et al. The melanocortin receptors and their accessory proteins. Front Endocrinol (Lausanne) 4:9 (2013).
Richardson et al. Synthesis and structure-activity relationships of novel arylpiperazines as potent and selective agonists of the melanocortin subtype-4 receptor. J Med Chem 47:744-755 (2004).
Science IP Report dated Mar. 29, 2018 (129 pgs).
Tian et al. Design, Synthesis, and Evaluation of Proline and Pyrrolidine Based Melanocortin Receptor Agonists. A Conformationally Restricted Dipeptide Mimic Approach. J Med Chem 49:4745-4761 (2006).
Tran et al. Syntheses of tetrahydrothiophenes and tetrahydrofurans and studies of their derivatives as melanocortin-4 receptor ligands. Bioorg Med Chem Lett 18:1124-1130 (2008).
Velentza et al. Novel MC2R antagonists decrease cortisol in primary human adrenal cortical cells and corticosterone in an in vivo model of hypercortisolism. Poster presented at 13th Annual Peptide Therapeutics Symposium; Oct. 25-26, 2018; La Jolla, CA.
Webb et al. Minireview: The Melanocortin 2 Receptor Accessory Proteins. Mol Endocrinol 24(3):475-484 (Mar. 2010).
Young et al. Management of endocrine disease: Cushing's syndrome due to ectopic ACTH secretion: an expert operational opinion. Eur J Endocrinol 182(4):R29-R58 (2020).
Ansel et al.: Pharmaceutical Dosage Forms and Drug Delivery Systems. Seventh Edition, Lippincott Williams & Wilkins (1999).
CAS Registry No. 2851421-84-4; STN Entry date Nov. 9, 2022; 2-Pyridinecarboxamide, N-(3S)-1-azabicyclo[2.2.2]oct-3-yl-6-(2-ethoxyphenyl)-3-[(2R)-2-ethyl-4-[1-(trifluoromethyl)cyclobutyl]carbonyl]-1-piperazinyl]-, (2Z)-2-butenedioate (1:1).
Co-pending U.S. Appl. No. 18/541,289, inventors Zhao; Yuxin et al., filed on Dec. 15, 2023.
International Conference on Harmonization of Technical Requirements for Registration of Pharmaceuticals for Human Use (ICH). Impurities: Guidelines for Residual Solvents Q3C(R6) 40 pages (Nov. 2005).
Nguyen et al. In Vitro Pharmacological Characterization of CRN04894: The First Reported Oral, Selective Nonpeptide Melanocortin 2 Receptor Antagonist Evaluated in Phase 1 First-in-Human Clinical Trials. FASEB J 36(S1):Abstract (2022).
Parween et al., Metformin inhibits the activation of melanocortin receptors 2 and 3 in vitro: A possible mechanism for its anti-androgenic and weight balancing effects in vivo? J Steroid Biochem Mol Biol. 200:105684 (2020).
PCT/US2023/084242 International Search Report and Written Opinion dated Mar. 28, 2024.
Sebhat et al., Melanocortin subtype 4 receptor agonists: Structure-activity relationships about the 4-alkyl piperidine core. Bioorg. Med. Chem. Lett. 17:5720-5723 (2007).
Cuevas-Ramos, Daniel. et al. Update on medical treatment for Cushing's disease. Clinical Diabetes and Endocrinology 2:16, 1-13 (2016).
Fowler, Melissa A. et al. Effects of CRN04894, a nonpeptide orally bioavailable ACTH antagonist, on corticosterone in rodent models of ACTH excess. Journal of the Endocrine Society 5(Supplement_1):A167 (2021).

\* cited by examiner

MELANOCORTIN SUBTYPE-2 RECEPTOR (MC2R) ANTAGONIST FOR THE TREATMENT OF DISEASE

CROSS-REFERENCE TO RELATED APPLICATIONS

This application claims the benefit of U.S. Provisional Application No. 63/163,310 filed on Mar. 19, 2021, and U.S. Provisional Application No. 63/298,571 filed on Jan. 11, 2022, each of which is incorporated herein by reference in its entirety.

FIELD OF THE INVENTION

Described herein is a melanocortin subtype-2 receptor (MC2R) antagonist and methods of using the MC2R antagonist in the treatment of conditions, diseases, or disorders that would benefit from modulating melanocortin subtype-2 receptor activity, such as Cushing's disease, congenital adrenal hyperplasia, and ectopic ACTH syndrome.

BACKGROUND OF THE INVENTION

The melanocortin receptors form a family of G protein-coupled receptor (GPCRs) (MC1R, MC2R, MC3R, MC4R, and MC5R) that are selectively activated by different melanocortin peptides, adrenocorticotropic hormone (ACTH), and the melanocortin peptides α-, β-, and γ-melanocyte-stimulating hormone (α-MSH, β-MSH, and γ-MSH), that are all derived proteolytically from proopiomelanocortin hormone, or POMC. ACTH is a 39 amino acid peptide that is the primary regulator of adrenal glucocorticoid synthesis and secretion and only has affinity for MC2R. As the central actor in this hypothalamic-pituitary-adrenal (HPA) axis, ACTH is secreted by the pituitary in response to stressful stimuli and acts at the adrenal gland to stimulate the synthesis and secretion of cortisol. Modulation of MC2R is attractive for the treatment of conditions, diseases, or disorders that would benefit from modulating melanocortin receptor activity.

SUMMARY OF THE INVENTION

Provided herein are methods for the treatment of diseases of excess adrenocorticotropic hormone (ACTH).

In one aspect, described herein is a method of treating Cushing's disease, congenital adrenal hyperplasia (CAH), ectopic ACTH syndrome (EAS), or a combination thereof, in a human, the method comprising administering to the human in need thereof a compound having the structure of Compound 1, or a pharmaceutically acceptable salt, or solvate thereof:

In some embodiments, the human produces excess ACTH. In some embodiments, the human has a pituitary adenoma or corticotroph adenoma. In some embodiments, the human has an ectopic ACTH-secreting tumor. In some embodiments, the human has a genetic mutation within the adrenal gland that results in impaired cortisol synthesis. In some embodiments, the human has a mutation in the gene encoding 21β-hydroxylase, 11β-hydroxylase, 17α-hydroxylase, 3β-hydroxysteroid dehydrogenase, and p450 oxidoreductase, or a combination thereof. In some embodiments, the human was administered or is currently administered an exogenous corticosteroid. In some embodiments, the exogenous corticosteroid is a glucocorticoid.

In some embodiments, treating Cushing's disease, CAH, EAS, or a combination thereof comprises reducing levels of ACTH-stimulated cortisol, androstenedione (A4), 17-hydroxyprogesterone (17-OHP), aldosterone, dehydroepiandrosterone sulfate (DHEAS), dehydroepiandrosterone (DHEA), or a combination thereof, in the human.

In some embodiments, treating Cushing's disease or EAS, or a combination thereof comprises reducing levels of cortisol in the human. In some embodiments, treating Cushing's disease or EAS, or a combination thereof comprises reducing levels of cortisol in the blood, serum, saliva, or urine or the human. In some embodiments, treating Cushing's disease or EAS, or a combination thereof comprises reducing cortisol levels to the average level of a human without Cushing's disease or EAS, or a combination thereof.

In some embodiments, treating CAH comprises reducing levels of steroids, androgens, steroid precursors, or combinations thereof, in the human. In some embodiments, treating CAH comprises reducing levels of A4, 17-OHP, or a combination thereof, in the human.

In some embodiments, the human with Cushing's disease or ectopic ACTH syndrome (EAS) has a non-pituitary tumor that secretes excessive amounts of ACTH, wherein the non-pituitary tumor is in the lungs, pancreas, thyroid, thymus gland, intestines, adrenal gland, or paraganglia.

In some embodiments, treating Cushing's disease or EAS comprises reducing growth of fat pads (collarbone, back of neck, face and trunk), excessive sweating, dilation of capillaries, thinning of the skin, muscle weakness, hirsutism, depression/anxiety, hypertension, osteoporosis, insulin resistance, hyperglycemia, heart disease, lethargy, obesity, menstrual irregularity, or combinations thereof.

In another aspect, described herein is a method of treating congenital adrenal hyperplasia (CAH) in a human, the method comprising administering to the human in need thereof, a compound having the structure of Compound 1, or a pharmaceutically acceptable salt, or solvate thereof:

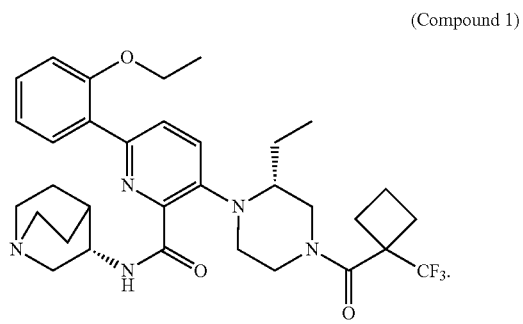 [SMILES: CCOc1ccccc1-c1ccc(N2CCN(C(=O)C3(C(F)(F)F)CCC3)C[C@H]2CC)c(C(=O)N[C@@H]2CN3CCC2CC3)n1]

(Compound 1)

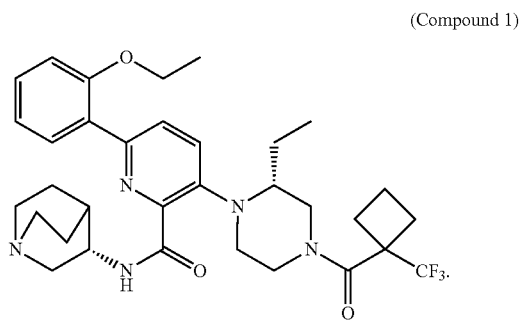

(Compound 1)

In some embodiments, the human has a genetic mutation that result in impaired cortisol synthesis. In some embodiments, the human has a mutation in the gene encoding 21β-hydroxylase, 11β-hydroxylase, 17α-hydroxylase, 3β-hydroxysteroid dehydrogenase, and p450 oxidoreductase, or a combination thereof.

In some embodiments, wherein the CAH is classical CAH. In some embodiments, the classical CAH comprises salt-losing CAH or simple-virilizing CAH.

In some embodiments, the CAH is non-classical CAH.

In some embodiments, treating CAH comprises reducing levels of ACTH-stimulated androstenedione (A4), 17-hydroxyprogesterone (17-OHP), aldosterone, dehydroepiandrosterone sulfate (DHEAS), dehydroepiandrosterone (DHEA), or a combination thereof, in the human. In some embodiments, treating CAH comprises reducing levels of ACTH-stimulated androgens or cortisol precursors in the human. In some embodiments, the androgens comprise androstenedione (A4). In some embodiments, the cortisol precursors comprise 17-hydroxyprogesterone (17-OHP). In some embodiments, treating CAH comprises reducing secretion of androgens.

In some embodiments, treating CAH comprises reducing incidence of improper gonadal development, hyperandrogenism, and replacement of mineralocorticoids. In some embodiments, the administration of Compound 1, or a pharmaceutically acceptable salt, or solvate thereof, comprises reducing exogenous glucocorticoid dose requirements for the human.

In another aspect, described herein is a method of reducing growth of fat pads (collarbone, back of neck, face and trunk), excessive sweating, dilation of capillaries, thinning of the skin, muscle weakness, hirsutism, depression/anxiety, hypertension, osteoporosis, insulin resistance, hyperglycemia, heart disease, lethargy, obesity, menstrual irregularity, or combinations thereof, in a human with congenital adrenal hyperplasia (CAH), the method comprising administering to the human in need thereof, a compound having the structure of Compound 1, or a pharmaceutically acceptable salt, or solvate thereof:

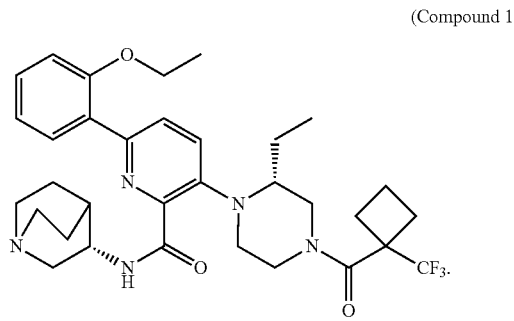

(Compound 1)

In some embodiments, the administration of Compound 1, or a pharmaceutically acceptable salt, or solvate thereof, comprises reducing exogenous glucocorticoid dose requirements for the human with CAH. In some embodiments, the exogenous glucocorticoid comprises beclomethasone, betamethasone, budesonide, cortisone, dexamethasone, hydrocortisone, methylprednisolone, prednisolone, prednisone, triamcinolone, or a combination thereof.

In another aspect, described herein is a method of reducing levels of ACTH-stimulated cortisol, androstenedione (A4), 17-hydroxyprogesterone (17-OHP), aldosterone, dehydroepiandrosterone sulfate (DHEAS), dehydroepiandrosterone (DHEA), or a combination thereof, levels in a human, the method comprising administering to the human in need thereof a compound having the structure of Compound 1, or a pharmaceutically acceptable salt, or solvate thereof:

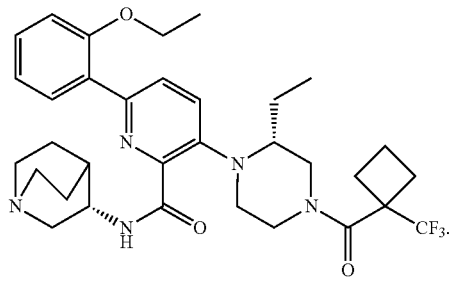

(Compound 1)

In some embodiments, the human has Cushing's disease, congenital adrenal hyperplasia (CAH), ectopic ACTH syndrome (EAS), or a combination thereof.

In some embodiments, reducing levels of ACTH-stimulated cortisol, A4, 17-OHP, aldosterone, DHEAS, DHEA, or a combination thereof comprises treating Cushing's disease, CAH, EAS, or a combination thereof.

In some embodiments of the methods described herein, Compound 1, or a pharmaceutically acceptable salt, or solvate thereof, is administered orally administered once daily or twice daily. In some embodiments, Compound 1, or a pharmaceutically acceptable salt, or solvate thereof, is administered in amount equivalent to about 5 mg to about 300 mg of Compound 1. In some embodiments, Compound 1, or a pharmaceutically acceptable salt, or solvate thereof, is administered in amount equivalent to about 10 mg to about 250 mg of Compound 1. In some embodiments, Compound 1, or a pharmaceutically acceptable salt, or solvate thereof, is administered in amount equivalent to about: 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, or 300 mg of Compound 1.

In another aspect, described herein is a method of treating a disease or condition associated with excess ACTH in a human, the method comprising administering to the human in need thereof a selective non-peptide small molecule melanocortin 2 receptor (MC2R) antagonist, wherein the non-peptide small molecule MC2R antagonist is about 100-fold more selective for MC2R than for MC1R, MC3R, MC4R, MC5R, or any combination thereof. In some embodiments, administration of the selective non-peptide small molecule MC2R antagonist to the human with excess ACTH comprises a suppression or reduction of ACTH-mediated pathological elevations of adrenal steroid hormones. In some embodiments, administration of the selective non-peptide small molecule MC2R antagonist to the human with excess ACTH comprises a suppression or reduction of adrenally derived cortisol and androgens. In some embodiments, administration of the selective nonpeptide small molecule MC2R antagonist to the human with excess ACTH comprises a suppression or reduction of adrenally derived cortisol and androgens and does not substantially affect mineralocorticoid production.

In some embodiments, the human has elevated cortisol levels. In some embodiments, the elevated cortisol levels are ACTH-dependent. In some embodiments, the human has a pituitary adenoma or corticotroph adenoma. In some embodiments, the human has an ectopic ACTH-secreting tumor.

In some embodiments, treating the disease or condition associated with excess ACTH comprises reducing levels of ACTH-stimulated cortisol, androstenedione (A4), 17-hydroxyprogesterone (17-OHP), aldosterone, dehydroepiandrosterone sulfate (DHEAS), dehydroepiandrosterone (DHEA), or a combination thereof, in the human. In some embodiments, treating disease associated with excess ACTH comprises reducing levels of cortisol in the human.

In some embodiments, the disease or condition associated with excess ACTH comprises Cushing's disease, congenital adrenal hyperplasia (CAH), ectopic ACTH syndrome (EAS), or a combination thereof.

In another aspect, described herein is a method of treating Cushing's disease, congenital adrenal hyperplasia (CAH), ectopic ACTH syndrome (EAS), or a combination thereof, in a human comprising administering to the human a therapeutically effective amount of a selective non-peptide small molecule MC2R antagonist, or a pharmaceutically acceptable salt, or solvate thereof, wherein the cortisol level in the human is reduced by at least 10% from baseline. In some embodiments, said cortisol level in the human is reduced by at least 10% from baseline and is maintained at a reduced level for at least 4 hours.

In some embodiments, wherein the CAH is classical CAH.

In some embodiments, the classical CAH comprises salt-losing CAH or simple-virilizing CAH.

In some embodiments, the CAH is non-classical CAH.

In some embodiments of the methods described herein, the selective non-peptide small molecule MC2R antagonist is a compound having the structure of Compound 1, or a pharmaceutically acceptable salt, or solvate thereof:

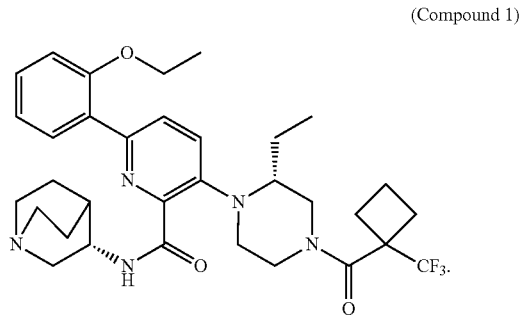 [SMILES: CCOc1ccccc1-c1ccc(N2CCN(C(=O)C3(C(F)(F)F)CCC3)C[C@H]2CC)c(C(=O)N[C@@H]2CN3CCC2CC3)n1]

(Compound 1)

In some embodiments, Compound 1, or a pharmaceutically acceptable salt, or solvate thereof, is administered orally administered once daily or twice daily. In some embodiments, Compound 1, or a pharmaceutically acceptable salt, or solvate thereof, is administered in amount equivalent to about 5 mg to about 300 mg of Compound 1. In some embodiments, Compound 1, or a pharmaceutically acceptable salt, or solvate thereof, is administered in amount equivalent to about 10 mg to about 250 mg of Compound 1.

In some embodiments, Compound 1, or a pharmaceutically acceptable salt, or solvate thereof, is administered in amount equivalent to about: 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, or 300 mg of Compound 1.

Articles of manufacture, which include packaging material, Compound 1, or a pharmaceutically acceptable salt thereof, within the packaging material, and a label that indicates that Compound 1, or a pharmaceutically acceptable salt thereof, is used for modulating the activity of a melanocortin receptor (e.g. melanocortin subtype-2 receptor (MC2R)), or for the treatment, prevention or amelioration of one or more symptoms of a disease or condition that would benefit from modulation of the activity of a melanocortin receptor (e.g. melanocortin subtype-2 receptor (MC2R)), are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION

Figure 1:
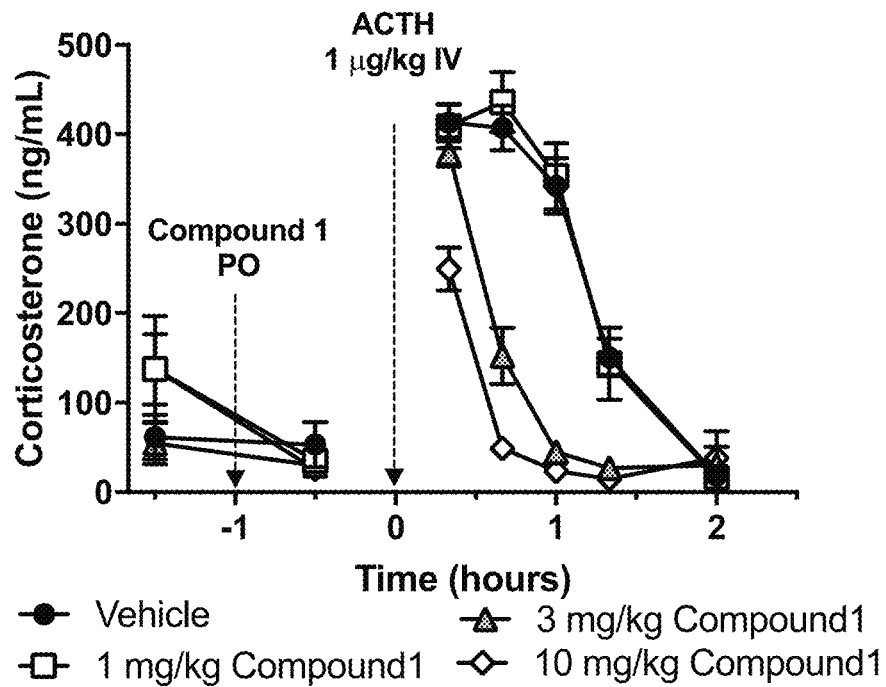
FIG. 1 shows the effect of a single dose of Compound 1 on corticosterone levels in male rats after administration of a single dose of ACTH(1-24).
Figure 1:
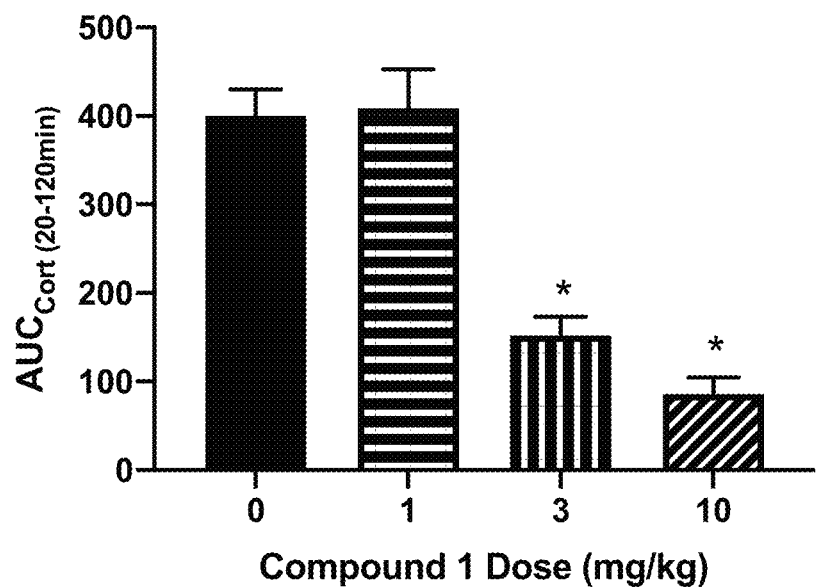

Adrenocorticotropic hormone (ACTH) is a 39 amino acid peptide synthesized by anterior pituitary corticotrophic cells by proteolytic cleavage of the proopiomelanocortin hormone (POMC). ACTH is the primary regulator of adrenal glucocorticoid (GC; cortisol in humans and most other species; corticosterone in rodents) synthesis and secretion. As the central actor in this hypothalamic-pituitary-adrenal (HPA) axis, ACTH is secreted by the pituitary in response to stressful stimuli and acts at the adrenal gland to stimulate the synthesis and secretion of cortisol. This stimulation is mediated through a highly specific G protein-coupled receptor (GPCR) which is expressed almost uniquely in the adrenal cortex. The receptor is the melanocortin 2 receptor (MC2R), and, along with ACTH, is part of the larger melanocortin system.

The melanocortin system comprises a family of five GPCRs (MC1R, MC2R, MC3R, MC4R, and MC5R); their natural agonists, the melanocortin peptides α-, β-, and γ-melanocyte-stimulating hormone (α-MSH, β-MSH, and γ-MSH) and ACTH; and endogenous melanocortin antagonists agouti and agouti-related protein (AGRP). The melanocortin receptors (MCRs) have different selectivities for endogenous agonist and antagonist peptides and are expressed in diverse tissues where they serve varied and discreet physiological functions (Gantz, I. and T. M. Fong, *Am. J. Physiol. Endocrinol. Metab.*, 284: E468-E474, 2003).

It is possible to selectively modulate any one of the MCRs, or combinations thereof. In some embodiments, selectively modulating any one of the MCRs relative to the other MCRs, or combinations thereof, is useful in a variety of clinical applications. In some embodiments, selectively modulating any one of the MCRs relative to the other MCRs, or combinations thereof, reduces unwanted side effects in a variety of clinical applications. In one aspect, compounds described herein are antagonists of MC2R. In some embodiments, compounds described herein are selective antagonists for MC2R relative or other MCRs.

MC2R is a highly selective receptor for ACTH. Although ACTH can activate all five MCRs, at physiological levels, the sensitivity of the other receptors is not high enough to be activated, and ACTH selectively activates MC2R. Importantly, the other naturally occurring agonists α-MSH, β-MSH, and γ-MSH have no affinity for MC2R (Gantz, I. and T. M. Fong, *Am. J. Physiol. Endocrinol. Metab.*, 284: E468-E474, 2003). The major function of MC2R is to stimulate the fasciculata cells of the adrenal cortex to synthesize and secret cortisol. MC2R requires the GPCR accessory protein MRAP (melanocortin 2 receptor protein) to be successfully secreted to the cell surface and as well as to function. MRAP is a small protein with a single transmembrane domain that forms an antiparallel homodimer in stable complex with MC2R and is necessary for both cell surface expression of MC2R and its ability to bind ACTH. MRAP can bind to any of the MCRs and affect their activities, but is only essential for MC2R activity. Binding of ACTH to the MC2R/MRAP complex on adrenal cortical cells activates Gs to elevate intracellular cAMP levels which in turn stimulates cortisol synthesis and secretion by regulating multiple steps in the steroidogenic pathway.

Cushing's Disease

Cushing's syndrome (CS) is a rare disorder characterized by chronic, excess exposure to elevated levels of glucocorticoids, particularly cortisol. Clinical signs of Cushing's syndrome include growth of fat pads (collarbone, back of neck, face and trunk), excessive sweating, dilation of capillaries, thinning of the skin, muscle weakness, hirsutism, depression/anxiety, hypertension, osteoporosis, insulin resistance, hyperglycemia, heart disease, and a range of other metabolic disturbances resulting in high morbidity. If inadequately controlled in its severe forms, Cushing's syndrome is associated with high mortality. Although glucocorticoid excess can sometimes be ACTH-independent, for example from excessive autonomous secretion of cortisol from a hyperfunctioning adrenal adenoma, carcinoma, or steroid abuse, about 60-80% of all cases are ACTH-dependent Cushing's syndrome, known as Cushing's disease (CD).

Cushing's disease is caused by pituitary corticotropic cell tumors that secrete excess ACTH, which, in turn, causes the downstream synthesis and over-secretion of cortisol by the adrenal glands. Cortisol is the body's main stress hormone and excess amounts can cause significant increases in mortality and morbidity. Corticotroph adenomas are small, usually slow growing, benign tumors that normally come to clinical attention as a result of the effects of glucocorticoid excess, rather than because of the physical effects of an expanding tumor. CD presents much more commonly in women, and usually between 30 and 50 years of age. CD often takes many years to diagnose with an estimated diagnosis time of 38 months, and may well be under-diagnosed in the general population as many of its symptoms such as lethargy, depression, obesity, hypertension, hirsutism and menstrual irregularity can be incorrectly attributed to other more common disorders. Cushing's disease is an orphan indication with a prevalence of approximately 10,000 patients in the United States.

First-line therapy for Cushing's disease is surgical and involves removal of either the ACTH-secreting tumor in the pituitary or, in severe cases, the adrenal glands themselves. As surgery is often unsuccessful, contraindicated, or delayed, pharmacological therapy for these patients becomes necessary. Adrenal enzyme inhibitors (e.g., metyrapone and ketoconazole) prevent the synthesis of cortisol and can improve symptoms but suffer from mechanistic side effects as a result of accumulation of precursor steroids. For example, metyrapone is associated with hirsutism in women and patients must be monitored carefully to avoid hypoadrenalism, hypokalemia, and hypertension. Ketoconazole often requires progressively increasing dosage to maintain disease control, but this is ultimately limited by the hepatotoxicity of the drug. In addition, it is a potent inhibitor of one of the most important drug metabolizing enzymes in the liver, CYP3A4, resulting in the potential for negative drug-interactions as a side effect. Mifepristone, a potent glucocorticoid receptor antagonist, is approved for control of hyperglycemia in Cushing's syndrome, but is difficult to titrate and has significant liabilities due to its potent anti-progesterone activity. The recently approved somatostatin analog, pasireotide, inhibits ACTH secretion, but in a recently published study, only 15-26% of patients in a Phase 3 trial achieved normalization of urinary free cortisol while 73% of patients experienced a hyperglycemia-related adverse event due to the compound's potent inhibition of insulin secretion.

In some embodiments, Compound 1, or a pharmaceutically acceptable salt, or solvate thereof, is used in the treatment of Cushing's disease. In some embodiments, Compound 1, or a pharmaceutically acceptable salt, or solvate thereof, is used in the treatment of glucocorticoid excess in Cushing's disease. In some embodiments, glucocorticoid excess in Cushing's disease is ACTH-dependent.

Ectopic ACTH Syndrome

Ectopic ACTH syndrome (EAS), or ectopic Cushing's syndrome or disease, is a rare disorder that results from non-pituitary tumors that secrete excessive amounts of ACTH. In many instances, these tumors occur in the lungs. In some instances, ectopic tumors occur in the pancreas, thyroid, and thymus. In some instances, ectopic tumors occur in the intestine. In some instances, ectopic tumors occur on the adrenal gland, such as with a pheochromocytoma. In some instances, ectopic tumors occur in paraganglia. In some instances, ectopic tumors occur in another organ. In some instances, ectopic tumors are cancerous. The supraphysiological degree of ACTH secretion in EAS can vary with effects that range from cushingoid to acutely life-threatening. In some embodiments, the tumors are small carcinoid tumors that occur anywhere in the lungs or gastrointestinal tract.

Treatment options for EAS are limited, with the first goal being surgical removal of the tumors, if possible. If surgery is not an option, medical therapy may be used to block cortisol production. And in some cases, adrenalectomy is required if the tumor cannot be located and medical therapy does not fully block the cortisol production.

In some embodiments, Compound 1, or a pharmaceutically acceptable salt, or solvate thereof, is used in the treatment of ectopic ACTH syndrome.

Congenital Adrenal Hyperplasia

Congenital adrenal hyperplasia (CAH) is characterized by a reduction or loss of cortisol synthesis and resultant excessive ACTH and corticotropin-releasing hormone due to loss of negative feedback by cortisol on the pituitary and hypothalamus. CAH encompasses a set of disorders that are caused by genetic mutations within the adrenal gland that result in impaired cortisol synthesis.

In some embodiments, CAH is due to a mutation in 21β-hydroxylase. Different mutations in the gene responsible for 21β-hydroxylase result in different levels of the enzyme, producing a spectrum of effects. CAH due to 21β-hydroxylase deficiency is responsible for 95% of all cases of CAH and is broken down further into two subcategories: classical CAH, including the salt-losing form and the simple-virilizing form; and non-classical CAH. In some instances, classical CAH can result in adrenal crisis and death if not detected and treated. In some instances, non-classical CAH is milder, and may or may not present symptoms. The lack of cortisol removes the negative feedback to the pituitary which leads to excessive ACTH secretion, which, in turn, causes overstimulation of the adrenal cortex. The resulting adrenal hyperplasia and over-secretion of other steroids (particularly androgens) and steroid precursors can lead to a variety of effects including improper gonadal development, hyperandrogenism, and life-threatening replacement of mineralocorticoids. CAH is an orphan indication with a prevalence of approximately 27,000 patients in the United States.

In other embodiments, CAH is due to a mutation in 11β-hydroxylase deficiency, 17α-hydroxylase deficiency, 3β-hydroxysteroid dehydrogenase deficiency, congenital lipoid adrenal hyperplasia, or p450 oxidoreductase deficiency which all present different symptoms.

The current treatment paradigm for CAH consists of lifelong daily glucocorticoid supplementation (e.g., hydrocortisone, prednisone, dexamethasone) which attempts to balance the inability to synthesize cortisol and alleviate the lack of negative feedback. In approximately ⅔ of patients with classic CAH due to 21β-hydroxylase deficiency, mineralocorticoid replacement is also necessary. In many instances, the dose of glucocorticoids required to suppress ACTH is in excess of physiologic replacement, and this excess exogenous glucocorticoid can result in Cushing's-like symptoms. Additionally, the inability to precisely dose glucocorticoids can often lead to cycles of over- or under-treatment. Under-treatment can result in adrenal crisis and stress doses of glucocorticoid for acute illness are common. Over-treatment can result in CS-like symptoms. CAH patients have a two-fold risk of bone fractures compared to the general population and commonly suffer from hypercholesterolemia, insulin resistance, and hypertension. Compared to the general population, CAH patients have a diminished life expectancy of 7 years, and more than 20% of CAH patients will die of a condition complicated by adrenal crisis.

In some embodiments, Compound 1, or a pharmaceutically acceptable salt, or solvate thereof, is used in the treatment of CAH. In some embodiments, Compound 1, or a pharmaceutically acceptable salt, or solvate thereof, is used in the treatment of CAH related to hyperandrogenism. In some embodiments, Compound 1, or a pharmaceutically acceptable salt, or solvate thereof, is used in the treatment of Cushing's-like symptoms caused by excessive exogenous glucocorticoid dosing in the treatment of CAH.

Compound 1

Compound 1 is a potent oral, non-peptide, small molecule MC2R antagonist ($K_i$<10 nM) that is >2900-fold selective over other human melanocortin receptor subtypes.

Compound 1 refers to 6-(2-ethoxyphenyl)-3-((R)-2-ethyl-4-(1-(trifluoromethyl)cyclobutane-1-carbonyl)piperazin-1-yl)-N—((S)-quinuclidin-3-yl)picolinamide, which has the chemical structure shown below.

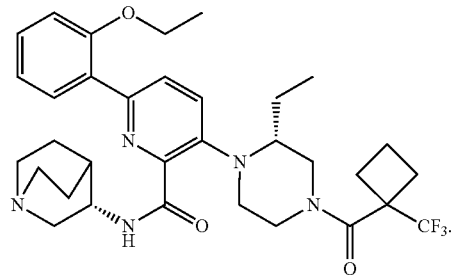

(Compound 1)

Compound 1 is also referred to as N-[(3S)-1-azabicyclo[2.2.2]octan-3-yl]-6-(2-ethoxyphenyl)-3-[(2R)-2-ethyl-4-[1-(trifluoromethyl)cyclobutanecarbonyl]piperazin-1-yl]pyridine-2-carboxamide.

Methods of Treatment

In certain aspects, disclosed herein is a method of reducing endogenous adrenocorticotropic hormone (ACTH)

activity in a human comprising administering to the human in need thereof Compound 1, or a pharmaceutically acceptable salt, or solvate thereof. In some embodiments, the method comprises reducing activity of ACTH on the adrenal gland. In some embodiments, the method comprises reducing downstream signaling of ACTH on the adrenal gland. In some embodiments, disclosed herein is a method of reducing endogenous cortisol levels in a human comprising administering to the human in need thereof Compound 1, or a pharmaceutically acceptable salt, or solvate thereof. In some embodiments, disclosed herein is a method of reducing endogenous adrenal steroid hormone levels in a human comprising administering to the human in need thereof Compound 1, or a pharmaceutically acceptable salt, or solvate thereof. In other aspects, disclosed herein is a method of inhibiting cortisol secretion from the adrenal glands in a human comprising administering to the human in need thereof Compound 1, or a pharmaceutically acceptable salt, or solvate thereof. In still other aspects, disclosed herein is a method of inhibiting adrenal androgen secretion and cortisol precursor production in a human comprising administering to the human in need thereof Compound 1, or a pharmaceutically acceptable salt, or solvate thereof. In some embodiments, the androgen is androstenedione (A4). In some embodiments, the cortisol precursor is 17 hydroxyprogesterone (17-OHP). In some embodiments, the human has a disease associated with excess adrenocorticotropic hormone (ACTH). In some embodiments, the human has Cushing's disease. In some embodiments, the human has CAH. In some embodiments, the human has EAS.

In certain aspects, disclosed herein is a method of reducing cortisol levels in a human with a disease associated with excess adrenocorticotropic hormone (ACTH), the method comprising administering to the human in need thereof, Compound 1, or a pharmaceutically acceptable salt, or solvate thereof. In certain embodiments, the method comprises reducing endogenous cortisol levels. In other embodiments, the method comprises reducing ACTH-stimulated cortisol levels. In some embodiments, the disease associated with excess ACTH is Cushing's disease. In some embodiments, the disease associated with excess ACTH is CAH. In some embodiments, the disease associated with excess ACTH is EAS.

In certain aspects, disclosed herein is a method of decreasing cortisol levels in a human with Cushing's disease, the method comprising administering to the human in need thereof, Compound 1, or a pharmaceutically acceptable salt, or solvate thereof. In certain aspects, disclosed herein is a method of decreasing cortisol levels in a human with CAH, the method comprising administering to the human in need thereof, Compound 1, or a pharmaceutically acceptable salt, or solvate thereof. In certain aspects, disclosed herein is a method of decreasing cortisol levels in a human with EAS, the method comprising administering to the human in need thereof, Compound 1, or a pharmaceutically acceptable salt, or solvate thereof. In certain aspects, disclosed herein is a method of decreasing cortisol levels in a human with CAH that has Cushing's-like symptoms, the method comprising administering to the human in need thereof, Compound 1, or a pharmaceutically acceptable salt, or solvate thereof. In certain embodiments, the method comprises reducing endogenous cortisol levels. In other embodiments, the method comprises reducing ACTH-stimulated cortisol levels.

In some embodiments, the methods disclosed herein comprise a method of treating a disease associated with excess ACTH. In some embodiments, the disease comprises excess cortisol levels. In some embodiments, the treatment comprises reducing cortisol levels. In some embodiments, the treatment comprises reducing endogenous cortisol levels. In some embodiments, the treatment comprises reducing ACTH-stimulated cortisol levels. In some embodiments, the disease associated with excess ACTH is Cushing's disease. In some embodiments, the disease associated with excess ACTH is CAH. In some embodiments, the disease associated with excess ACTH is EAS.

In some embodiments, treating Cushing's syndrome, including Cushing's disease, comprises treating one or more symptoms of Cushing's syndrome. In some embodiments, treating Cushing's syndrome, including Cushing's disease, comprises reducing growth of fat pads (collarbone, back of neck, face and trunk), excessive sweating, dilation of capillaries, thinning of the skin, muscle weakness, hirsutism, depression/anxiety, hypertension, osteoporosis, insulin resistance, hyperglycemia, heart disease, lethargy, obesity, menstrual irregularity, or combinations thereof. In some embodiments, treating Cushing's syndrome, including Cushing's disease, comprises reducing growth of fat pads (collarbone, back of neck, face and trunk). In some embodiments, treating Cushing's syndrome, including Cushing's disease, comprises reducing excessive sweating. In some embodiments, treating Cushing's syndrome, including Cushing's disease, comprises reducing dilation of capillaries. In some embodiments, treating Cushing's syndrome, including Cushing's disease, comprises reducing thinning of the skin. In some embodiments, treating Cushing's syndrome, including Cushing's disease, comprises reducing muscle weakness. In some embodiments, treating Cushing's syndrome, including Cushing's disease, comprises reducing hirsutism. In some embodiments, treating Cushing's syndrome, including Cushing's disease, comprises reducing depression/anxiety. In some embodiments, treating Cushing's syndrome, including Cushing's disease, comprises reducing hypertension. In some embodiments, treating Cushing's syndrome, including Cushing's disease, comprises reducing osteoporosis. In some embodiments, treating Cushing's syndrome, including Cushing's disease, comprises reducing insulin resistance.

In some embodiments, treating Cushing's syndrome, including Cushing's disease, comprises reducing hyperglycemia. In some embodiments, treating Cushing's syndrome, including Cushing's disease, comprises reducing heart disease. In some embodiments, treating Cushing's syndrome, including Cushing's disease, comprises reducing lethargy. In some embodiments, treating Cushing's syndrome, including Cushing's disease, comprises reducing obesity. In some embodiments, treating Cushing's syndrome, including Cushing's disease, comprises reducing menstrual irregularity.

In some embodiments, treating CAH comprises reducing improper gonadal development, hyperandrogenism, and replacement of mineralocorticoids. In some embodiments, treating CAH comprises reducing improper gonadal development. In some embodiments, treating CAH comprises reducing hyperandrogenism. In some embodiments, treating CAH comprises reducing replacement of mineralocorticoids.

In some embodiments, the methods described herein comprise reducing levels of at least one metabolite. In some embodiments, the metabolite is an ACTH-stimulated metabolite. In some embodiments, the metabolite comprises cortisol, A4, 17-OHP, dehydroepiandrosterone sulfate (DHEAS), dehydroepiandrosterone (DHEA), or a combination thereof. In some embodiments, the methods comprise reducing levels of endogenous cortisol. In some embodiments, the methods comprise reducing ACTH-stimulated cortisol, A4, 17-OHP, aldosterone, DHEAS, DHEA, or a combination thereof. In some embodiments, the metabolite is reduced compared to the level of the metabolite in the subject before treatment. In some embodiments, the metabolite is reduced by at least about 5%, 10%, 15%, 20%, 25%, 30%, 35%, 40%, 45%, 50%, or more than 50%.

In some embodiments, the methods described herein comprises reducing the level of cortisol. In some embodiments, the methods comprise reducing levels of endogenous cortisol. In some embodiments, the levels of endogenous cortisol are reduced in the blood, serum, saliva, or urine. In some embodiments, the methods comprise reducing ACTH-stimulated cortisol. In some embodiments, the levels of ACTH-stimulated cortisol are reduced in the blood, serum, saliva, or urine. In some embodiments, blood cortisol levels are reduced. In some embodiments, serum cortisol levels are reduced. In some embodiments, salivary levels are reduced. In some embodiments, urine free cortisol (UFC) levels are reduced. In some embodiments, the levels of cortisol are reduced as determined by an ACTH-stimulation test. In some embodiments, the levels of cortisol are reduced by at least about 5%, 10%, 15%, 20%, 25%, 30%, 35%, 40%, 45%, 50%, or more than 50%. In some embodiments, the levels of cortisol in blood, serum, saliva, or urine are reduced by at least about 5%, 10%, 15%, 20%, 25%, 30%, 35%, 40%, 45%, 50%, or more than 50%. In some embodiments, the levels of cortisol are reduced compared to the levels of cortisol before treatment. In some embodiments, the levels of cortisol are reduced to that of a human without one of the diseased described herein. That is, in some embodiments, the levels of cortisol are restored to a normal level in the human.

Subjects

In some embodiments, the subject is a human.

In some embodiments, the subject has a disease associated with excess ACTH. In some embodiments, the subject has Cushing's disease. In some embodiments, the subject has CAH. In some embodiments, the subject has EAS. In some embodiments, the subject has Cushing's-like symptoms caused by excessive exogenous glucocorticoid dosing in the treatment of CAH.

In some embodiments, the human has excess cortisol. In some embodiments, the human has elevated cortisol levels. In some instances, a human without elevated cortisol levels has cortisol levels of about 10-20 mcg/dL in blood or 50-100 mcg/day in a 24-hour urinary cortisol test. In some embodiments, the human has a cortisol level higher than about 20 mcg/dL, 25 mcg/dL, 30 mcg/dL, or more in blood. In some embodiments, the human has 24-hour urinary cortisol levels higher than about 50 mcg/day, 100, mcg/day, 150 mcg/day, 200 mcg/day or more in a 24-hour urinary cortisol test.

In some embodiments, the human has 24-hour urinary cortisol excretion higher than the upper limit of normal (ULN) for a human. In some embodiments, the human has 24-hour urinary cortisol excretion at least 1.5-fold, 2.0-fold, 2.5-fold or more of ULN. In some embodiments, the ULN for 24-hour urinary cortisol excretion is about 50-55 mcg/day.

In some embodiments, the human has late night salivary cortisol level higher than the ULN for a human. In some embodiments, the human has late night salivary cortisol level at least 1.5-fold, 2.0-fold, 2.5-fold or more of ULN. In some embodiments, the ULN for late night salivary cortisol level is about 100 ng/dL.

In some embodiments, the human has elevated serum cortisol in the low dose dexamethasone suppression test. In some embodiments, the human has serum cortisol level of 1.8 mcg/dL or higher the morning following night-time administration of 1 mg of dexamethasone.

In some embodiments, the human has an excess of cortisol that is ACTH-dependent. In some embodiments, the human has an excess of ACTH. In some instances, a human without elevated ACTH levels has about 10-50 pg/mL in blood. In some embodiments, the human has an ACTH level higher than about 50 pg/mL, 75 pg/mL, 100 pg/mL, or more in blood.

In some embodiments, the human was administered or is currently administered an exogenous corticosteroid. In some embodiments, the human was administered or is currently administered an exogenous corticosteroid, wherein the exogenous corticosteroid is a glucocorticoid. In some embodiments, the human was administered or is currently administered an exogenous corticosteroid, wherein the exogenous corticosteroid is an oral, injectable, or inhaled corticosteroid. In some embodiments, the human has been exposed to exogenous glucocorticoids. In some embodiments, the human has been exposed to exogenous glucocorticoids over a sustained period of time to treat an acute or chronic condition in the human. In some embodiments, the exogenous glucocorticoid is an oral, injectable, or inhaled corticosteroid. In some embodiments, the exogenous glucocorticoid is beclomethasone, betamethasone, budesonide, cortisone, dexamethasone, hydrocortisone, methylprednisolone, prednisolone, prednisone, triamcinolone, or the like. In some embodiments, the exogenous glucocorticoid has been used to treat inflammatory diseases, such as rheumatoid arthritis, lupus, or asthma; joint pain, bursitis, back pain; or skin disorders, such as eczema, in the human. In some embodiments, the human has CAH and has been exposed to exogenous glucocorticoids. In some such embodiments, the human with CAH shows Cushing's-like symptoms.

In some embodiments, the human produces excess ACTH. In some embodiments, the human has a pituitary gland tumor (pituitary adenoma) or corticotroph adenoma. In some embodiments, the pituitary adenoma or corticotroph adenoma is benign. In other embodiments, the human has an ectopic ACTH-secreting tumor. In other embodiments, the human has an ACTH-secreting tumor in an organ that does not normally produce ACTH. In some embodiments, the ACTH-secreting tumor is in the lungs, pancreas, thyroid, thymus gland, intestines, adrenal gland, or paraganglia. In some embodiments, the ACTH-secreting tumor is cancerous. In some embodiments, the ACTH-secreting tumor is benign.

In some embodiments, the human has a mutation in a genetic loci affecting cortisol synthesis. The most common mutations (approximately 95%) occur at the genes that encode the 21β-hydroxylase, and result in a 21β-hydroxylase deficiency. More rare causes include gene mutations in the genes that encode 11β-hydroxylase, 17α-hydroxylase, 3β-hydroxysteroid dehydrogenase, and p450 oxidoreductase. In some embodiments, the human has a mutation in the gene encoding 21β-hydroxylase, 11β-hydroxylase, 17α-hydroxylase, 3β-hydroxysteroid dehydrogenase, and p450 oxidoreductase, or a combination thereof.

Dosage and Administration

In one embodiment, Compound 1, or a pharmaceutically acceptable salt, or solvate thereof, are used in the preparation of medicaments for the treatment of a disease associated with excess ACTH. Methods for treating any of the diseases or conditions described herein in a subject in need of such treatment, involves administration of pharmaceutical compositions that include at least Compound 1 or a pharmaceutically acceptable salt, active metabolite, prodrug, or pharmaceutically acceptable solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a subject, who previously experienced at least one symptom of the disease being treated and is currently in remission, a pharmaceutical composition comprising Compound 1, or a pharmaceutically acceptable salt, or solvate thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In some embodiments, Compound 1, or a pharmaceutically acceptable salt, or solvate thereof, is administered orally to the human. In some embodiments, Compound 1, or a pharmaceutically acceptable salt, or solvate thereof, is administered to the human on a continuous dosing schedule. In some embodiments, Compound 1, or a pharmaceutically acceptable salt, or solvate thereof, is administered to the human on a continuous daily dosing schedule.

The term "continuous dosing schedule" refers to the administration of a particular therapeutic agent at regular intervals. In some embodiments, continuous dosing schedule refers to the administration of a particular therapeutic agent at regular intervals without any drug holidays from the particular therapeutic agent. In some other embodiments, continuous dosing schedule refers to the administration of a particular therapeutic agent in cycles. In some other embodiments, continuous dosing schedule refers to the administration of a particular therapeutic agent in cycles of drug administration followed by a drug holiday (for example, a wash out period or other such period of time when the drug is not administered) from the particular therapeutic agent. For example, in some embodiments the therapeutic agent is administered once a day, twice a day, three times a day, once a week, twice a week, three times a week, four times a week, five times a week, six times a week, seven times a week, every other day, every third day, every fourth day, daily for a week followed by a week of no administration of the therapeutic agent, daily for a two weeks followed by one or two weeks of no administration of the therapeutic agent, daily for three weeks followed by one, two or three weeks of no administration of the therapeutic agent, daily for four weeks followed by one, two, three or four weeks of no administration of the therapeutic agent, weekly administration of the therapeutic agent followed by a week of no administration of the therapeutic agent, or biweekly administration of the therapeutic agent followed by two weeks of no administration of the therapeutic agent. In some embodiments, daily administration is once a day. In some embodiments, daily administration is twice a day. In some embodiments, daily administration is three times a day. In some embodiments, daily administration is more than three times a day.

The term "continuous daily dosing schedule" refers to the administration of a particular therapeutic agent every day at roughly the same time each day. In some embodiments, daily administration is once a day. In some embodiments, daily administration is twice a day. In some embodiments, daily administration is three times a day. In some embodiments, daily administration is more than three times a day.

In some embodiments, the amount of Compound 1, or a pharmaceutically acceptable salt, or solvate thereof, is administered once-a-day.

In certain embodiments wherein improvement in the status of the disease or condition in the human is not observed, the daily dose of Compound 1, or a pharmaceutically acceptable salt, or solvate thereof, is increased. In some embodiments, a once-a-day dosing schedule is changed to a twice-a-day dosing schedule. In some embodiments, three times a day dosing schedule is employed to increase the amount of a Compound 1, or a pharmaceutically acceptable salt, or solvate thereof, that is administered. In some embodiments, the frequency of administration is increased in order to provide maintained or more regular exposure to an ACTH antagonist (e.g. Compound 1, or a pharmaceutically acceptable salt thereof). In some embodiments, the frequency of administration is increased in order to provide repeat high Cmax levels on a more regular basis and/or provide maintained or more regular exposure to an ACTH antagonist (e.g. Compound 1, or a pharmaceutically acceptable salt thereof).

In any of the aforementioned aspects are further embodiments comprising single administrations of the effective amount of an ACTH antagonist (e.g. Compound 1, or a pharmaceutically acceptable salt thereof), including further embodiments in which the ACTH antagonist, is administered (i) once a day; or (ii) multiple times over the span of one day.

In any of the aforementioned aspects are further embodiments comprising multiple administrations of the effective amount of an ACTH antagonist (e.g. Compound 1, or a pharmaceutically acceptable salt thereof), including further embodiments in which (i) the ACTH antagonist is administered continuously or intermittently: as in a single dose; (ii) the time between multiple administrations is every 6 hours; (iii) the ACTH antagonist is administered to the mammal every 8 hours; (iv) the ACTH antagonist is administered to the mammal every 12 hours; (v) the ACTH antagonist is administered to the mammal every 24 hours. In further or alternative embodiments, the method comprises a drug holiday, wherein the administration of the ACTH antagonist is temporarily suspended or the dose of the ACTH antagonist being administered is temporarily reduced; at the end of the drug holiday, dosing of the ACTH antagonist is resumed. In one embodiment, the length of the drug holiday varies from 2 days to 1 year.

In general, however, doses of Compound 1 employed for adult human treatment are typically in the range of 0.01 mg-500 mg per day. In one embodiment, the desired dose is conveniently presented in a single dose or in divided doses administered simultaneously or at appropriate intervals, for example as two, three, four or more sub-doses per day.

In some embodiments, Compound 1, or a pharmaceutically acceptable salt, or solvate thereof, is administered in an amount equivalent to about 5 mg to about 300 mg of Compound 1. In some embodiments, Compound 1, or a pharmaceutically acceptable salt, or solvate thereof, is administered in an amount equivalent to about 5 mg to about 250 mg of Compound 1. In some embodiments, Compound 1, or a pharmaceutically acceptable salt, or solvate thereof, is administered in an amount equivalent to about 10 mg to about 250 mg of Compound 1.

In some embodiments, Compound 1, or a pharmaceutically acceptable salt, or solvate thereof, is administered in amount equivalent to about: 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, or 300 mg of Compound 1. In some embodiments, Compound 1, or a pharmaceutically acceptable salt, or solvate thereof, is administered in amount equivalent to about 40 mg of Compound 1. In some embodiments, Compound 1, or a pharmaceutically acceptable salt, or solvate thereof, is administered in amount equivalent to about 80 mg of Compound 1. In some embodiments, Compound 1, or a pharmaceutically acceptable salt, or solvate thereof, is administered in amount equivalent to about 120 mg of Compound 1. In some embodiments, Compound 1, or a pharmaceutically acceptable salt, or solvate thereof, is administered in amount equivalent to about 160 mg of Compound 1.

In some embodiments, Compound 1, or a pharmaceutically acceptable salt, or solvate thereof, is administered in a dose of at least about: 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, or 300 mg of Compound 1.

In some embodiments, Compound 1, or a pharmaceutically acceptable salt, or solvate thereof, is administered in a dose of no more than about: 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, or 300 mg of Compound 1.

In one embodiment, the daily dosages appropriate for the compound of Compound 1, or a pharmaceutically acceptable salt, or solvate thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in subjects, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

Treatment Based on Biomarker Detection

In some embodiments, the administration of pharmaceutical compositions that include Compound 1, or a pharmaceutically acceptable salt, or solvate thereof, is based on the patient's circulating cortisol levels, androstenedione (A4) levels, 17-hydroxyprogesterone (17-OHP) levels, aldosterone levels, dehydroepiandrosterone sulfate (DHEAS) levels, dehydroepiandrosterone (DHEA) levels, or a combination thereof.

In some embodiments, Compound 1, or a pharmaceutically acceptable salt, or solvate thereof, is administered via a titration schedule. In some embodiments, Compound 1, or a pharmaceutically acceptable salt, or solvate thereof, is administered via a titration schedule to minimize adverse events associated with the administration of Compound 1, or a pharmaceutically acceptable salt, or solvate thereof. In some embodiments, titration with Compound 1, or a pharmaceutically acceptable salt, or solvate thereof, enables: a subject to tolerate Compound 1, or a pharmaceutically acceptable salt, or solvate thereof; to minimize adverse events associated with the administration of Compound 1, or a pharmaceutically acceptable salt, or solvate thereof; maximizes the likelihood that an optimized dose of Compound 1, or a pharmaceutically acceptable salt, or solvate thereof, will be administered to the subject and tolerated; or a combination thereof. In some embodiments, titration comprises one or more cycles of dose escalation (i.e. up-titration), dose de-escalation (i.e. down-titration), or combination thereof. In some embodiments, titration comprises up-titration.

As used herein, a subject is said to "tolerate" a dose of a compound if administration of that dose to that subject does not result in an unacceptable adverse event or an unacceptable combination of adverse events. One of skill in the art will appreciate that tolerance is a subjective measure and that what may be tolerable to one patient may not be tolerable to a different patient.

As used herein, an "adverse event" is an untoward medical occurrence that is associated with treatment with Compound 1, or a pharmaceutically acceptable salt, or solvate thereof.

As used herein, an "optimized dose" refers a therapeutic dose optimized to the needs of a specific subject and is the highest dose of Compound 1, or a pharmaceutically acceptable salt, or solvate thereof, that is equivalent to the highest dose of Compound 1, that elicits the biological or medicinal response in the subject that is being sought and that can be tolerated by the subject, as determined by the subject, optionally in consultation with the subject's healthcare practitioner. In some embodiments, once an "optimized dose" is determined the optimized dose is administered to the subject so long as treatment is needed (i.e. the optimized dose is a maintenance dose).

In some embodiments, the titration schedule for Cushing's disease and/or EAS is based on rate of cortisol changes, individual tolerability, and improvement in disease signs and symptoms. In some embodiments, the titration schedule for Cushing's disease and/or EAS is based on urine free cortisol (UFC) levels. In some embodiments, the titration schedule for Cushing's disease and/or EAS is based on rate of change of urine free cortisol (UFC) levels.

As used herein, "up-titration" of a compound refers to increasing the amount of a compound until the subject does not tolerate the increased amount. Up-titration can be achieved in one or more dose increments, which may be the same or different. In some embodiments, the method comprises administering Compound 1, or a pharmaceutically acceptable salt, or solvate thereof, at an initial dose once daily for an initial period of time followed by up-titration to a higher dose of Compound 1, or a pharmaceutically acceptable salt, or solvate thereof, once daily thereafter. In some embodiments, the initial period of time comprises one day, about one week, about two weeks, about three weeks, about four weeks, about five weeks, about six weeks, about seven weeks, about eight weeks, about nine weeks, about ten weeks, about eleven weeks, or about 12 weeks. In some embodiments, this cycle is repeated until an optimized dose is achieved.

In some embodiments, the method of titration comprises administering Compound 1, or a pharmaceutically acceptable salt, or solvate thereof, at an initial dose once or twice daily for about one week, about two weeks, about three weeks, about four weeks, about five weeks, about six weeks, about seven weeks, or about eight weeks, followed by up-titration to a higher dose of Compound 1, or a pharmaceutically acceptable salt, or solvate thereof, once or twice daily thereafter. In some embodiments, this cycle is repeated until an optimized dose is achieved.

In some embodiments, the method of titration comprises administering Compound 1, or a pharmaceutically acceptable salt, or solvate thereof, at an initial dose once daily for about one week, about two weeks, about three weeks, about four weeks, about five weeks, about six weeks, about seven weeks, or about eight weeks, followed by up-titration to a higher dose of Compound 1, or a pharmaceutically acceptable salt, or solvate thereof, once daily thereafter. In some embodiments, this cycle is repeated until an optimized dose is achieved.

In some embodiments, the method of titration comprises the up-titration, or down-titration followed by an optional re-up-titration of Compound 1, or a pharmaceutically acceptable salt, or solvate thereof.

In some embodiments, the titration schedule comprises administering Compound 1, or a pharmaceutically acceptable salt or solvate thereof, at an initial dose for about one week and, provided that the patient tolerates the initial dose, increasing the dose by an amount equal to a first incremental value or provided that the patient does not tolerate the initial dose, decreasing the dose by an amount equal to a first incremental value.

In some embodiments, the titration schedule further comprises: administering Compound 1, or a pharmaceutically acceptable salt thereof, at the increased dose for about one week or two weeks and provided that the patient tolerates the increased dose, further increasing the dose by an amount equal to a second incremental value; or administering Compound 1, or a pharmaceutically acceptable salt thereof, at the decreased dose for about one week and provided that the patient tolerates the decreased dose, optionally increasing the dose by an amount equal to a second incremental value. In some embodiments, the first incremental value is the same as the second incremental value. In some embodiments, the first incremental value and the second incremental value are different.

In some embodiments of the titration scheme, doses of Compound 1, or a pharmaceutically acceptable salt or solvate thereof, are adjusted every week, every 2 weeks, every 3 weeks, or every 4 weeks.

In some embodiments of the titration scheme, doses of Compound 1, or a pharmaceutically acceptable salt or solvate thereof, are increased by an incremental value if the human has 24-hr urine free cortisol (UFC) levels >ULN.

In some embodiments of the titration scheme, doses of Compound 1, or a pharmaceutically acceptable salt or solvate thereof, are decreased if UFC levels fall below target range, and/or there is a rapid decrease in cortisol levels.

In some embodiments, an optimized dose is obtained when: 24-hr urine free cortisol (UFC) levels are no longer greater than ULN; 24-hr urine free cortisol (UFC) levels do not substantially change in response to treatment; or combination thereof.

In some embodiments, the initial dose of Compound 1, or a pharmaceutically acceptable salt, or solvate thereof, is equivalent to about 1 mg to about 300 mg of Compound 1. In some embodiments, the initial dose of Compound 1, or a pharmaceutically acceptable salt, or solvate thereof, is equivalent to about 1 mg to about 200 mg of Compound 1. In some embodiments, the initial dose of Compound 1, or a pharmaceutically acceptable salt, or solvate thereof, is equivalent to about 1 mg to about 100 mg of Compound 1. In some embodiments, the initial dose of Compound 1, or a pharmaceutically acceptable salt, or solvate thereof, is equivalent to about 1 mg to about 50 mg of Compound 1.

In some embodiments, the initial dose of Compound 1, or a pharmaceutically acceptable salt, or solvate thereof, is equivalent to about: 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, or 300 mg of Compound 1.

In some embodiments, the first incremental value is equivalent to about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 23 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, or about 50 mg of Compound 1.

In some embodiments, the second incremental value is equivalent to about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 23 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, or about 50 mg of Compound 1.

In some embodiments, the titration schedule is repeated until an optimized dose is obtained. An optimized dose provides efficacy of treatment while minimizes side effects with ACTH antagonist treatment.

In some embodiments, the optimized dose of Compound 1, or a pharmaceutically acceptable salt, or solvate thereof, is equivalent to about: 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, or 300 mg of Compound 1.

In some embodiments, the optimized dose is de-escalated when UFC levels fall below target range, and/or there is a rapid decrease in cortisol levels.

Combination Therapy

In certain instances, it is appropriate to administer at least Compound 1, or a pharmaceutically acceptable salt, or solvate thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, Compound 1, or a pharmaceutically acceptable salt, or solvate thereof, is co-administered with a second therapeutic agent, wherein the compound of Compound 1, or a pharmaceutically acceptable salt, or solvate thereof, and the second therapeutic agent modulate different aspects of the disease, disorder or condition being treated, thereby providing a greater overall benefit than administration of either therapeutic agent alone.

In one specific embodiment, Compound 1, or a pharmaceutically acceptable salt, or solvate thereof, is co-administered with a second therapeutic agent, wherein the second therapeutic agent is a glucocorticoid, a mineralocorticoid, or combination thereof. In some embodiments, administration of Compound 1, or a pharmaceutically acceptable salt, or solvate thereof, comprises reducing exogenous glucocorticoid dose requirements for the human. Example glucocorticoids contemplated for co-administration include, but are not limited to, beclomethasone, betamethasone, budesonide, cortisone, dexamethasone, ethamethasoneb, hydrocortisone, methylprednisolone, prednisolone, prednisone, triamcinolone, or the like. Example mineralocorticoids contemplated for co-administration include, but are not limited to, fludrocortisone and the like.

In some embodiments of the treatment of Cushing's disease or EAS, Compound 1, or a pharmaceutically acceptable salt, or solvate thereof, is co-administered with a second therapeutic agent, wherein the second therapeutic agent is a glucocorticoid (i.e. "block and replace" therapy). In some embodiments, the glucocorticoid is beclomethasone, betamethasone, budesonide, cortisone, dexamethasone, ethamethasoneb, hydrocortisone, methylprednisolone, prednisolone, prednisone, or triamcinolone. In some embodiments of the treatment of Cushing's disease or EAS, Compound 1, or a pharmaceutically acceptable salt, or solvate thereof, is co-administered with a low-dose glucocorticoid. In some embodiments, low-dose glucocorticoid comprises less than or equal to 20 mg/day prednisone equivalent. In some embodiments, low-dose glucocorticoid comprises less than or equal to 15 mg/day prednisone equivalent. In some embodiments, low-dose glucocorticoid comprises less than or equal to 10 mg/day prednisone equivalent. In some embodiments, low-dose glucocorticoid comprises less than or equal to 5 mg/day prednisone equivalent.

In any case, regardless of the disease, disorder or condition being treated, the overall benefit experienced by the patient is simply be additive of the two therapeutic agents or the patient experiences a synergistic benefit.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is Compound, or a pharmaceutically acceptable salt, or solvate thereof) are administered in any order or even simultaneously. If administration is simultaneous, the multiple therapeutic agents are, by way of example only, provided in a single, unified form, or in multiple forms (e.g., as a single pill or as two separate pills).

Compound 1, or a pharmaceutically acceptable salt, or solvate thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include oral administration.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

It should be understood that in addition to the ingredients particularly mentioned above, the compounds and compositions described herein may include other agents conventional in the art having regard to the type of formulation in question, for example those suitable for oral administration may include flavoring agents.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used in the specification and claims, the singular forms "a", "an" and "the" include plural references unless the context clearly dictates otherwise. For example, the term "a sample" includes a plurality of samples, including mixtures thereof.

As used herein, the term "about" a number refers to that number plus or minus 10% of that number. The term "about" a range refers to that range minus 10% of its lowest value and plus 10% of its greatest value.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), or a pharmaceutically acceptable salt thereof, and a co-agent, are both administered to a patient simultaneously in the form of a single entity or dosage. The term "non-fixed combination" means that the active ingredients, e.g. a compound of Formula (I), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The section headings used herein are for organizational purposes only and are not to be construed as limiting the subject matter described.

EXAMPLES

The following examples are included for illustrative purposes only and are not intended to limit the scope of the invention.

Example 1: Melanocortin Receptor (MCR) Assays

Inhibition of ACTH Binding:

Crude membrane fractions are prepared from CellSensor CRE-bla CHO-K1 cells stably expressing functional hMC2 receptor (ThermoFisher #K1483). The cells are cultured to 85-100% confluency in growth media [GlutaMax DMEM (Gibco #10569-010) supplemented with 10% dialyzed fetal bovine serum (Gemini Bio-Products #100-108), 0.1 mM non-essential amino acids (Gibco #11140-050), 100 U/mL penicillin; 100 µg/mL streptomycin; 2 mM L-glutamine (Gemini Bio-Products #400-110), 5 µg/mL blasticidin (GoldBio #B-800-100), 100 µg/mL zeocin (Invitogen #R25005) and 600 µg/mL hygromycin B (GoldBio #31282-04-9)]. Cells were collected and washed in Dulbecco's phosphate buffered saline (Corning #21-031-CV). The cell pellet is reconstituted in membrane preparation buffer [20 mM HEPES (Biopioneer #C0113), 6 mM $MgCl_2$ (Sigma #M8266) and 1 mM EDTA (JT Baker #4040-01), protease inhibitor tablets (Pierce #A32963); pH7.4)] and homogenized using a Dounce homogenizer. The membrane fraction is separated from cell debris and collected in membrane preparation buffer, flash frozen in liquid nitrogen and stored at −80° C.

The inhibition of binding to the human MC2R receptor was measured in a radioactive competition binding assay using the radiolabeled [$^{125}$I]-TYR$^{23}$]-ACTH (1-39) ligand (PerkinElmer #NEX083, custom synthesis) as the probe ligand for the receptor. Briefly, membranes from cells expressing the human MC2R were incubated with SPA beads (PerkinElmer #RPNQ0001) in binding assay buffer [50 mM HEPES (Biopioneer #C0113), 5 mM $MgCl_2$ (Sigma #M8266), 1 mM $CaCl_2$ (Fisher Scientific #BP510), 0.2%

BSA (Fisher Scientific #BP1600), and protease inhibitors (Pierce #A32963); pH 7.4]. Membranes bound to SPA bead were treated with various dilutions of compounds (final concentrations typically 0-10,000 nM), and 0.2 nM radiolabeled ligand in 96-well isoplates (PerkinElmer #6005040) for 90 minutes at room temperature. The radioactive signal was detected using a MicroBetaTriLux 1450 LSC (PerkinElmer). All data manipulations to determine the $K_i$ values were performed using GraphPad v8 (GraphPad, San Diego CA).

Compound 1 potently inhibits cAMP production via human MC2R (hMC2R) with an equilibrium inhibitory constant ($K_i$) in a binding assay of <10 nM. The selectivity over other human MCR subtypes was evaluated using commercially available MC1R, MC3R, MC4R, and MC5R membrane binding assays. The half maximal inhibitory concentration in the binding assays ($IC_{50}$) were determined to be greater than the highest concentration tested, or >10,000 nM, >1000 nM, >10,000 nM and >1000 nM for MC1R, MC3R, MC4R and MC5R, respectively. Compound 1 is >2900-fold selective for MC2R versus the other human MCRs.

Example 2: Off-Target Selectivity Panel

Compound 1 was tested at Eurofins Panlabs Discovery Services Taiwan, Ltd. for evaluation in their SafetyScreen™ panel of assays. This included selectivity assays at 87 targets including G-protein coupled receptors, nuclear receptors, other cell surface receptors, ion channels, enzymes, and transporters. Compound 1 was tested at a single concentration (10 µM) and showed little activity across the panel. Only the serotonin 5-hydroxytryptamine 1B receptor (5-HT$_{1B}$), calcium channel L-type (phenylalkylamine) and sodium channel (site 2) showed inhibition/activity >70% at this concentration.

A subsequent dose response of Compound 1 against the 5-HT$_{1B}$ receptor in the functional agonist and antagonist modes determined that Compound 1 had no agonistic activity (no signal up to 3000 nM) and weak antagonistic activity ($IC_{50}$ about 750 nM). The selectivity of Compound 1 for hMC2R over 5-HT$_{1B}$ is >2200-fold.

Example 3: Suppression of ACTH-Induced Corticosterone

The pharmacodynamic (PD) effects of Compound 1 were examined in rat by evaluating suppression of the corticosterone (cortisol in humans) response induced by administration of ACTH.
Single Oral Dose ACTH Challenge Test:

The ability of a single oral dose of Compound 1 to suppress corticosterone over 2 hours in response to an ACTH challenge test was assessed in male and female rats. Acute, IV administration of 1 µg/kg ACTH(1-24) induced a robust rise in plasma corticosterone levels compared to baseline in male and female rats. Oral administration of Compound 1 dose-dependently suppressed ACTH-stimulated corticosterone secretion.

Figure 2:
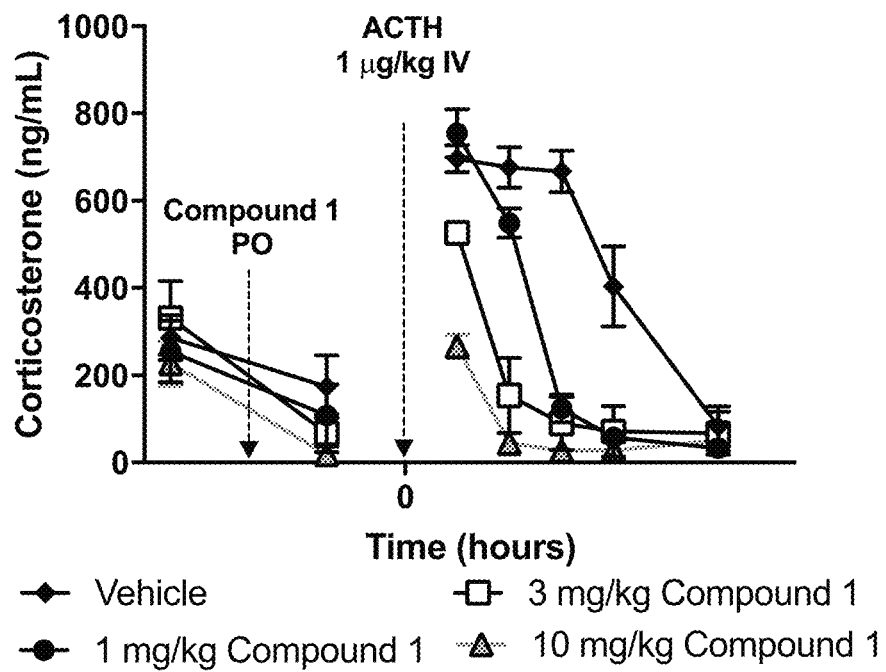
FIG. 2 shows the effect of a single dose of Compound 1 on corticosterone levels in female rats after administration of a single dose of ACTH(1-24).
Figure 2:
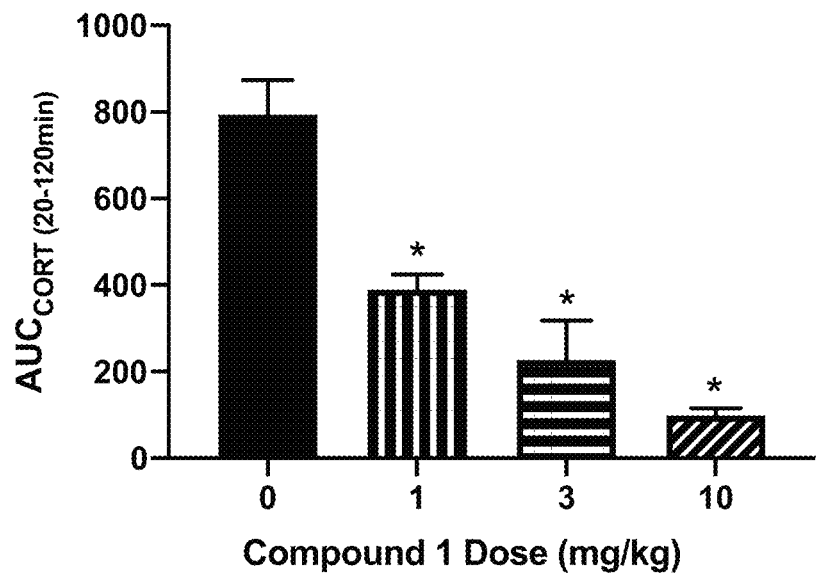

Statistically significant suppression of corticosterone was observed with ≥3 mg/kg Compound 1 in male rats (62% and 78% suppression with 3 and 10 mg/kg, respectively; FIG. 1) and ≥1 mg/kg Compound 1 in female rats (51%, 71%, and 88% suppression with 1, 3, and 10 mg/kg, respectively; FIG. 2) compared to vehicle treated rats. The minimum effective dose of orally administered Compound 1 determined in the 1 µg/kg ACTH-stimulated acute assay was 3 mg/kg in male rats and was associated with a $C_{max}$ of 149 ng/mL and an AUC up to the last measurable concentration ($AUC_{0-t}$) of 1400 ng·hr/mL.
Effect of Single Oral Dose with Repeated ACTH Challenges:

The ability of a single dose of Compound 1 to suppress corticosterone after repeated ACTH(1-24) (1 µg/kg) challenges was evaluated to determine the reproducibility of the ACTH-stimulated corticosterone response and the amount of time required to restore the corticosterone response to vehicle levels.

Figure 3:
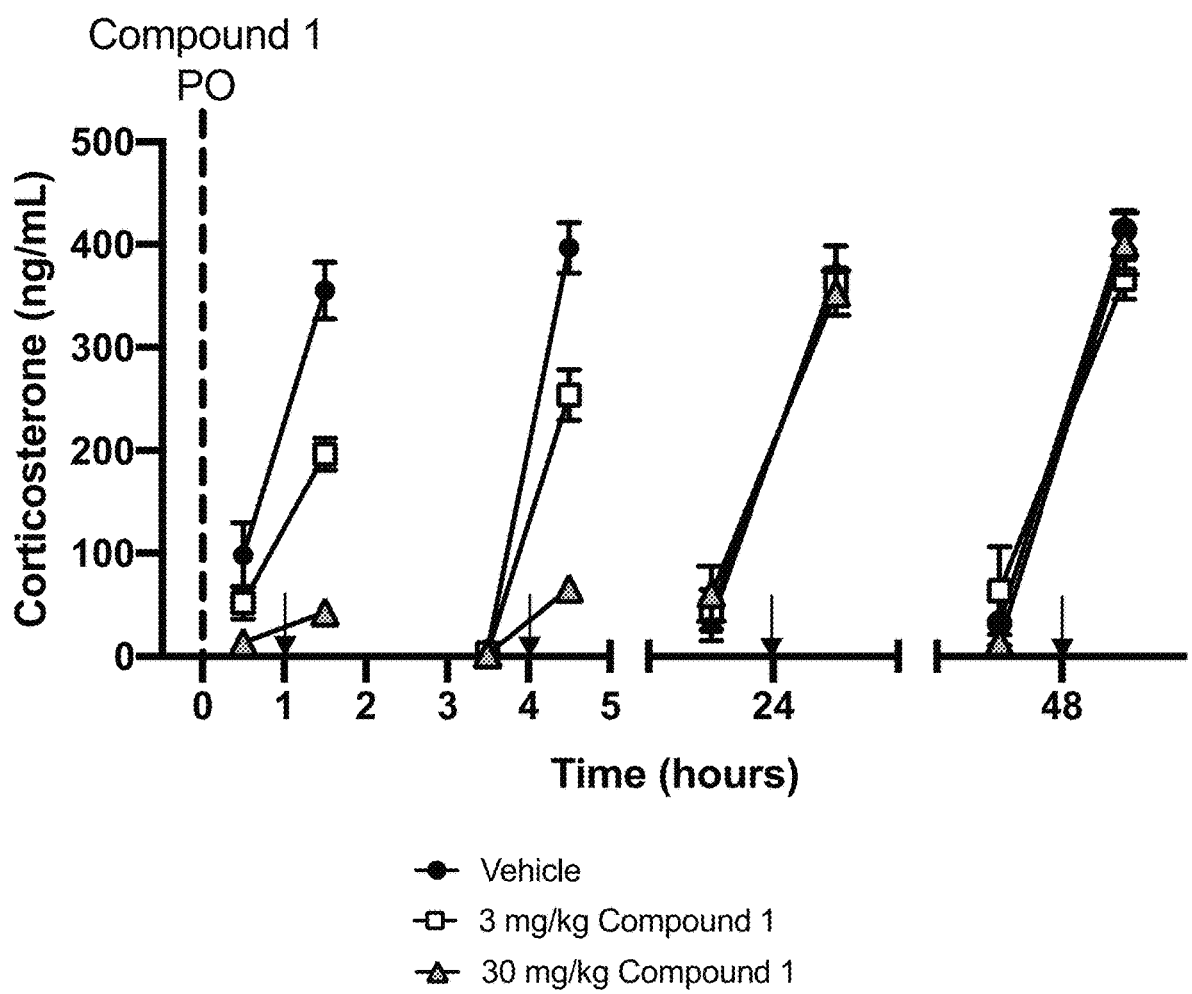
FIG. 3 shows the effect of a single dose of Compound 1 on corticosterone levels in rats after administration of a repeated doses of ACTH(1-24).

As shown in FIG. 3, after each ACTH stimulation test (at 1, 4, 24, and 48 hours post-Compound 1 dosing), corticosterone was reproducibly increased from baseline (<100 ng/mL) to >350 ng/mL in vehicle treated rats. Compound 1 suppressed ACTH-stimulated corticosterone at 1 hour (44% and 88% with 3 and 30 mg/kg, respectively) and 4 hours (36% and 84% with 3 and 30 mg/kg, respectively) post-oral administration compared to vehicle treatment. ACTH-stimulated corticosterone returned to normal, vehicle levels at 24 and 48 hours after a single oral administration of 3 or 30 mg/kg Compound 1.

Example 4: Suppression of ACTH-Induced Corticosterone in Animal Disease Models

Compound 1 was evaluated in disease models of excess ACTH and hypercortisolemia in rat and mouse.
Continuous Pump-Administration of ACTH:

Exogenous ACTH(1-24) (100 µg/kg/day) was administered to male rats via subcutaneously implanted osmotic pumps. The ability of repeated daily oral administration of Compound 1 to suppress corticosterone over 7 days was evaluated.

Figure 4:
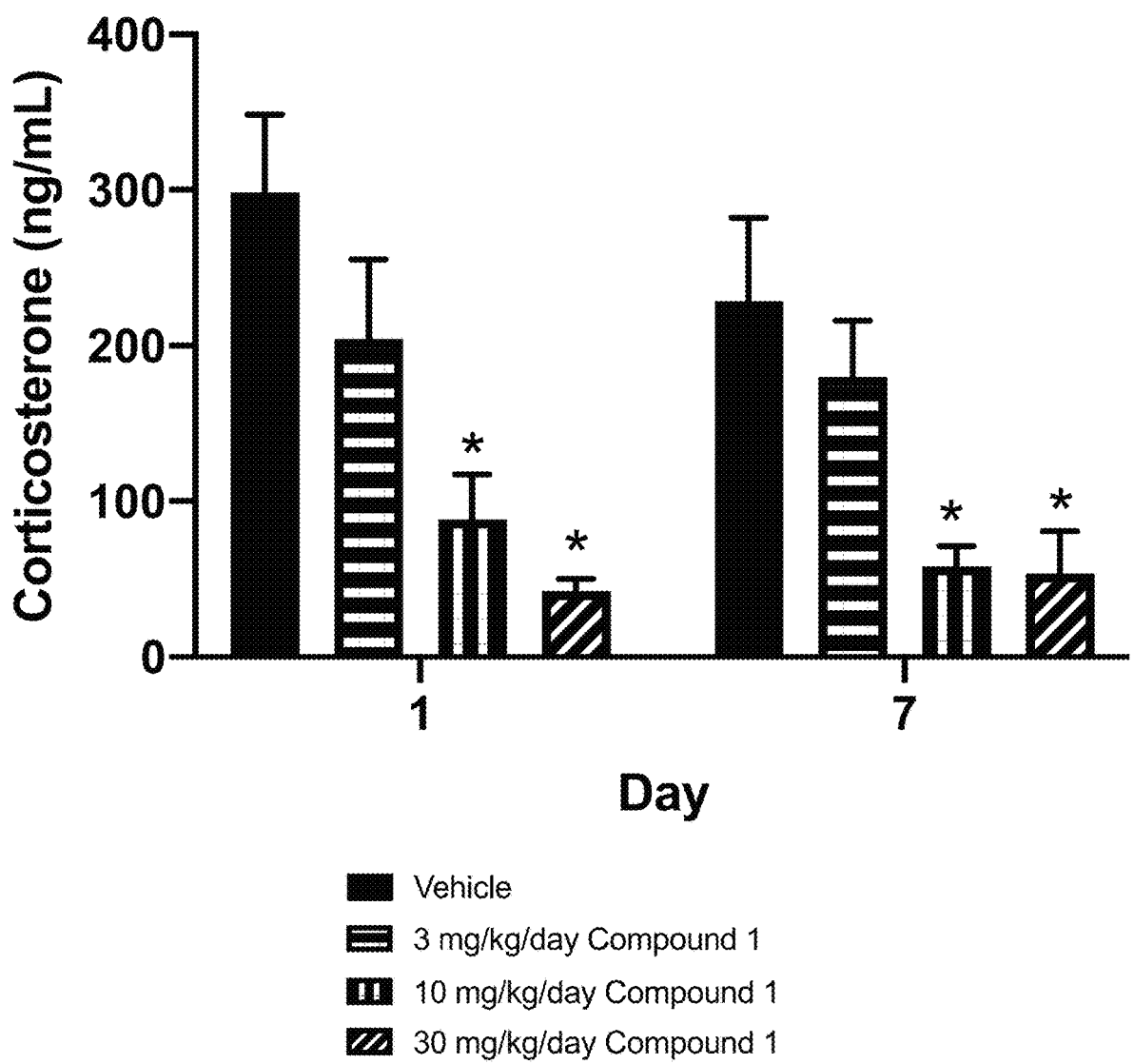
FIG. 4 shows the dose dependent suppression of corticosterone levels in rats continuously dosed ACTH(1-24) after repeated daily doses of Compound 1.

Compound 1 administered at ≥10 mg/kg/day dose-dependently suppressed corticosterone measured 1 hour post-dose on Day 1 and Day 7 (FIG. 4).

Figure 5:
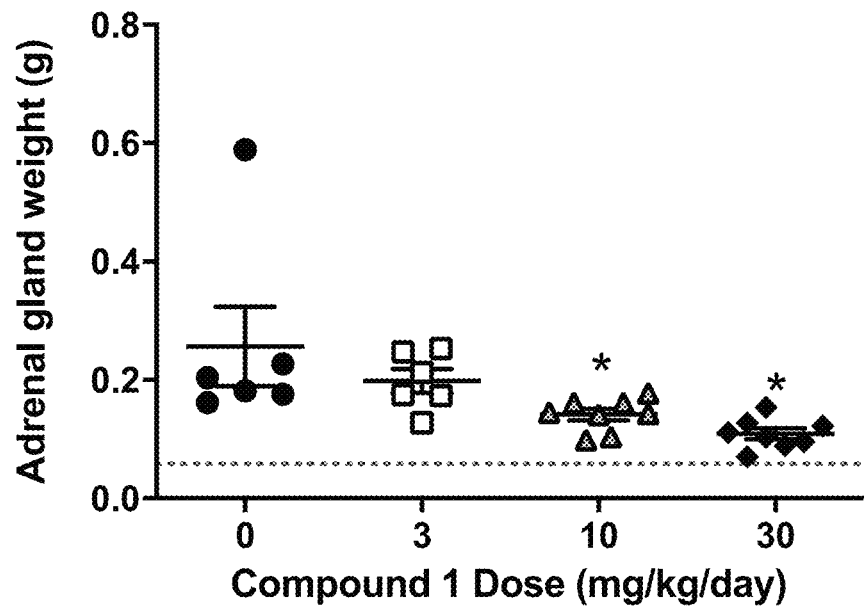
FIG. 5 shows the reduction in adrenal gland weight and adrenal cortical area in rats continuously dosed ACTH(1-24) after repeated daily doses of Compound 1.
Figure 5:
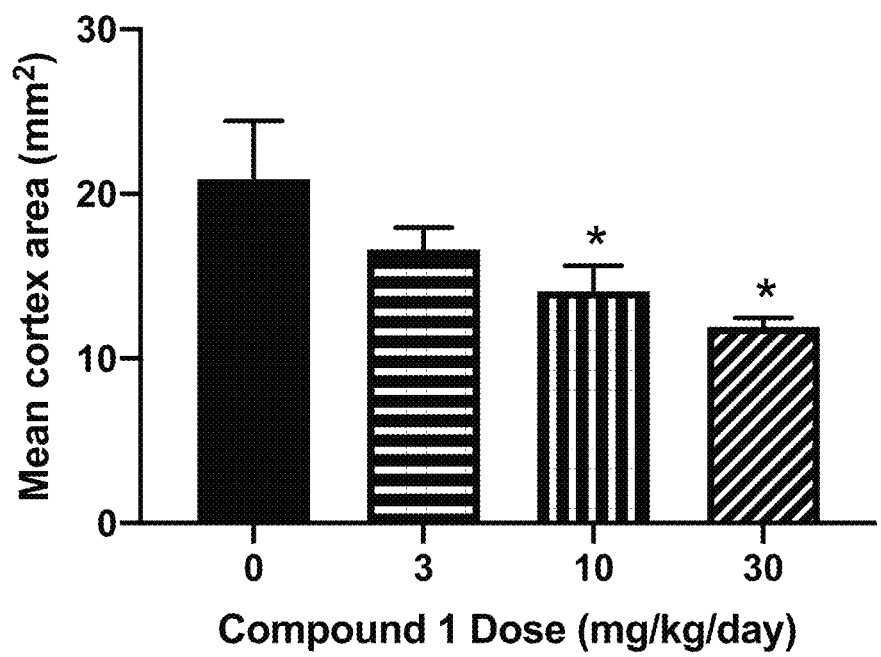

Additionally, Compound 1 ameliorated adrenal gland hypertrophy by reducing adrenal gland weight and adrenal cortical area in rats administered 10 and 30 mg/kg/day compared to vehicle treatment (FIG. 5).
ACTH-Secreting Mouse Pituitary Cell Tumor Model:

The ability of 14 days of daily oral administration of Compound 1 to suppress corticosterone in a mouse model of ACTH excess was evaluated.

Briefly, female Balb/c nude mice were subcutaneously implanted with AtT-20 corticotroph tumor cells in the rear flank (3 million cells/injection/animal) on Day 0. The no-tumor (NT) control group was injected with media only. When tumors became palpable on Day 21, mice were assigned to groups randomized for body weight, and 0, 15, 30 or 100 mg/kg/day of Compound 1. Compound 1 was orally administered for 14 days (Day 21 to Day 34).

Figure 6:
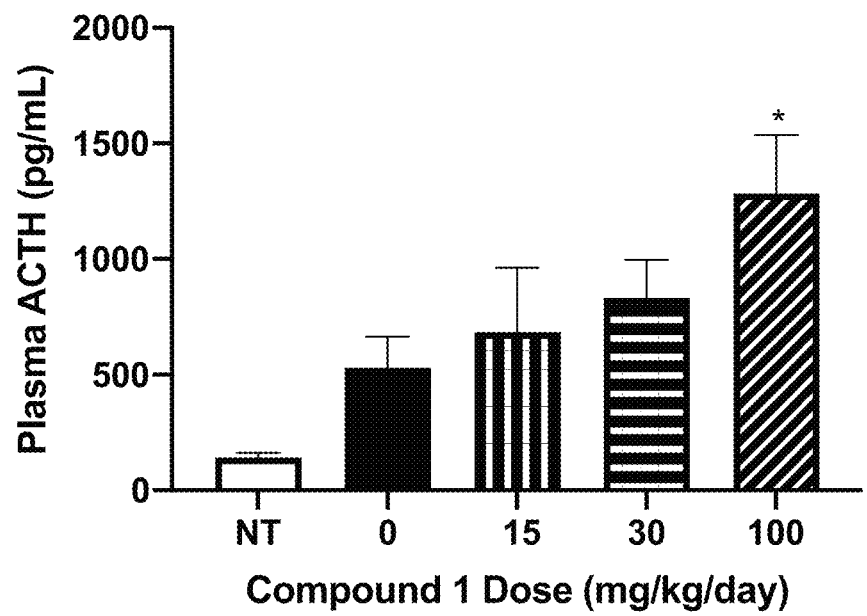
FIG. 6 shows the dose dependent suppression of corticosterone levels in rats with ACTH-secreting AtT-20 cell tumors after repeated daily doses of Compound 1.
Figure 6:
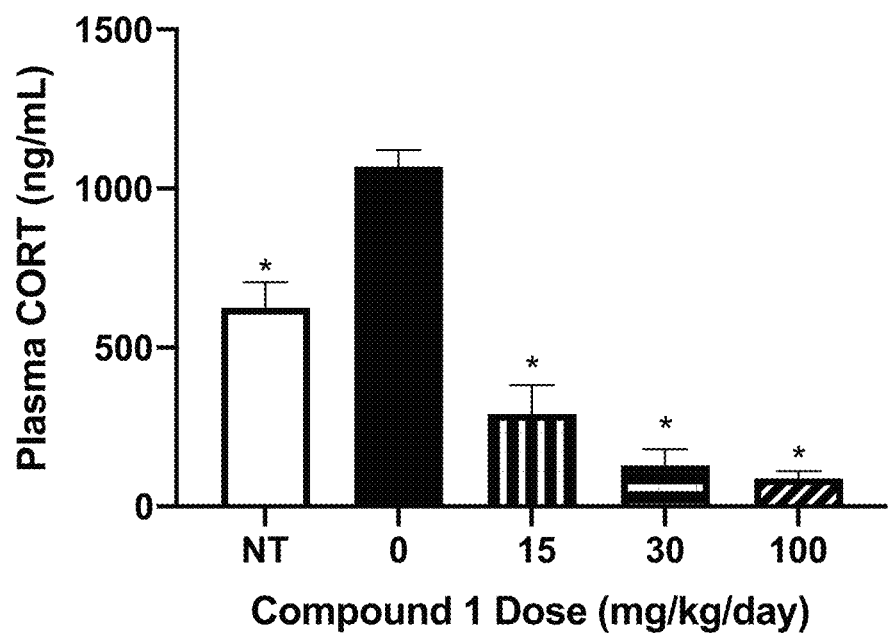

Daily oral dosing of Compound 1 had no significant effect on tumor volume or body weight over the course of the experiment. On Day 34, mice with subcutaneous implantation of ACTH-secreting AtT-20 corticotroph tumor cells had a 3.8-fold increase in plasma ACTH and a 1.7-fold increase in plasma corticosterone levels compared to mice receiving a sham injection of media only FIG. 6. Repeated oral administration of ≥15 mg/kg/day Compound 1 dose-dependently suppressed plasma corticosterone by 73%, 88%, and 92% with 15, 30, and 100 mg/kg/day Compound 1, respectively, compared to vehicle treatment in mice with ACTH-secreting AtT-20 cell tumors, as assessed 2 hours after administration on the last day of dosing. A 2.4-fold increase in ACTH levels was observed with 100 mg/kg/day Compound 1 compared to vehicle treatment.

Example 5: A Clinical Trial to Evaluate the Effects of Compound 1 on Adrenocorticotropic Hormone (ACTH) in Humans A non-limiting example of a clinical trial of an ACTH antagonist in humans is described below.

Purpose:

This Phase 1, first-in-human, double-blind, randomized, placebo-controlled study will evaluate the safety of Compound 1 in healthy volunteers as well as the relationship between exposure and pharmacodynamic (PD) parameters, including ACTH-stimulated and endogenous cortisol secretion measured in blood, saliva, and urine. Results will be used to inform endpoints and other parameters in future later studies in patients with Cushing's disease (CD) or other diseases of excess adrenocorticotropic hormone (ACTH), including Congenital Adrenal Hyperplasia (CAH) and Ectopic ACTH Syndrome (EAS).

Intervention:

Screening Period: Up to 28 days

Treatment Period: 1 day/single dose in the SAD; 10 days in the MAD

Assessment and Observation Period: 6 days in the SAD and 17 days in the MAD

Follow-up Period: at least 7 days after the last dose of study drug (planned: Day 8/SAD and Day 20/MAD)

SAD/Part 1: ascending single dose, randomized, placebo-controlled, double-blind; 5 planned and up to 8 total cohorts, n=64. In each cohort, 6 subjects will receive Compound 1, 2 subjects will receive the placebo. Doses will escalate from 10 mg in cohort 1 to no more than 250 mg.

MAD/Part 2: multiple ascending dose, randomized, placebo-controlled, double-blind; 2 planned and up to 4 total cohorts (n=36). In each cohort, 6 subjects will receive Compound 1, 3 subjects will receive the placebo. The doses will not exceed the doses in the SAD.

Inclusion Criteria:

Healthy male and female subjects ≥18 to ≤55 years of age, at time of Screening. Females must be either: postmenopausal for at least 12 months or surgically sterile; or agree to use a stable and permitted highly effective method of contraception from Screening until at least 30 days after the last dose of study drug. Males must be surgically sterile; or remain abstinent; or agree to use a spermicide-coated condom when sexually active with a female partner of childbearing potential from Screening until at least 30 days after the last dose of study drug. The female partner should also use a highly effective form of contraception during this same time period. Male subjects must also agree to not donate sperm for the duration of the study and until at least 90 days after the last dose of study drug.

A peak 30- or 60-minute ACTH-stimulated serum cortisol ≥18 µg/dL at Screening.

Exclusion Criteria:

Subjects will be excluded based on the following criteria: females who are pregnant or lactating; prior treatment with Compound 1; use of topical, nasal, inhaled, or oral corticosteroids within 3 days or 5 half-lives, whichever is longer, prior to the day of randomization or expected to require during the study; use of prohibited prescribed or non-prescribed medications and/or non-medications/alternative medicinal products within 7 days prior to Screening and is not willing to forego use of these substances during the study (unless otherwise specified); use of medications that are strong inducers of cytochrome P450 CYP3A4 within 30 days prior Screening of this trial or strong inhibitors of CYP3A4 within 14 days prior to Screening; use of any investigational drug within the past 60 days or 5 half-lives, whichever is longer, prior to Screening; any condition that in the opinion of the Investigator would jeopardize the subject's appropriate participation in this study.

Outcome Measures:

To evaluate the safety and tolerability of single and multiple doses of Compound 1.

To evaluate the PK of single and multiple doses of Compound 1.

To assess the PD effect of Compound 1 including suppression of ACTH-stimulated serum cortisol and adrenal androgen production, early morning serum cortisol, and adrenal androgen production.

In the MAD phase, 24-hour urine free cortisol (UFC) will be evaluated to collect initial dose-response data that may be used to inform dosing for later studies in Cushing's disease (CD) and ectopic ACTH syndrome (EAS).

In addition, the effect of Compound 1 on adrenal androgen and cortisol precursor secretion (including A4 and 17-OHP, respectively) will be assessed in both the SAD and MAD, which may be used to support dosing for later studies in congenital adrenal hyperplasia (CAH).

ACTH(1-39), which is elevated in the potential patient populations, will be measured at the timepoints specified to gain an understanding of the drug effects on endogenous ACTH.

ACTH-Stimulation Test

The ACTH-stimulation test is conducted on multiple study days throughout both phases of this study. This test is regarded as the diagnostic "gold standard" for diagnosis of adrenal insufficiency for its frequency of use and validation.

Initially, the ACTH-stimulation test is conducted at Screening to assess the hypothalamic pituitary-adrenal (HPA) axis as a safety element, i.e., to ensure the subject has sufficient adrenal function (as assessed by peak ACTH-stimulated cortisol secretion) prior to entering the trial. Additional ACTH-stimulation tests are conducted during the study to produce exogenous elevations in ACTH and resultant elevation in cortisol and androgens.

ACTH-stimulation tests are conducted while fasting. For PD analyses, blood samples are collected for measurement of serum cortisol, A4, 17-OHP, aldosterone, and DHEA. A summary of the procedure is as follows: In the "high dose" test, each subject is administered an IV 250 µg dose (for subjects >37 lbs) of cosyntropin (ACTH(1-24)) at the start of each test; in the "low dose" test, 1 mcg is administered instead. At 2 hours after study drug dosing/Time 0 (±5 minutes), collect blood sample. Within 5 minutes, administer cosyntropin IV infusion over 2 minutes. Collect blood sample at Time 30 minutes (5 minutes). Collect blood sample at Time 60 minutes (5 minutes).

SAD Blood Biomarkers

Endocrine biomarkers are assessed throughout the study.

Morning Biomarkers:

Starting on Day −1 until EOS (or ET), fasting pre-dose blood samples are collected <15 minutes prior to dosing (~0800 hr) for measurement of serum cortisol, A4, 17-OHP, aldosterone, ACTH(1 39), renin, and DHEAS. On Days in which ACTH-stimulation tests are conducted, these tests are done approximately 2 hours post-study drug dosing. Prior to cosyntropin administration, at 2 hours (15 minutes) post-dose, blood samples are collected for measurement of cortisol, A4, 17-OHP, aldosterone, and DHEA. Cosyntropin is then administered to define time 0 of the ACTH-stimulation test. At 2.5 hours (15 minutes) post-dose/30 minutes post-cosyntropin, blood samples are collected for measurement of cortisol. At 3 hours (15 minutes) post-dose/60 minutes post-cosyntropin, blood samples are collected for measurement of cortisol, A4, 17-OHP, aldosterone, and DHEA.

Mid-Day Biomarker:

On Days −1, 1, and 2, fasting blood samples are collected for measurement of serum cortisol at 4 hours (15 minutes) post-dose (~1200 hr). On the days in which the ACTH-stimulation test is conducted, this collection will be 120 min post-cosyntropin administration, such that post-cosyntropin cortisol collection times are Time 30 minutes (5 minutes), Time 60 minutes (5 minutes), and Time 120 minutes (5 minutes).

MAD Blood Biomarkers

Endocrine biomarkers are assessed throughout the study to assess what, if any, the role the circadian cycle plays.

Morning Biomarkers:

Starting on Day −1 until EOS (or ET), fasting pre-dose blood samples are collected <15 minutes prior to dosing for measurement of serum cortisol, A4, 17-OHP, aldosterone, ACTH(1 39), renin, and DHEAS. On Days in which ACTH-stimulation tests is conducted, these tests are done approximately 2 hours post-study drug dosing. Prior to cosyntropin administration, at 2 hours (15 minutes) post-dose, blood samples are collected for measurement of cortisol, A4, 17-OHP, aldosterone, and DHEA. Cosyntropin is then administered (250 mcg in the "high dose" test; 1 mcg in the "low dose" test) to define time 0 of the ACTH-stimulation test. At 2.5 hours (±15 minutes) post-dose/30 minutes post-cosyntropin, blood samples are collected for measurement of cortisol. At 3 hours (15 minutes) post-dose/60 minutes post-cosyntropin, blood samples are collected for measurement of cortisol, A4, 17-OHP, aldosterone, and DHEA.

Mid-Day Biomarker:

At Screening and on Days 2, 3, 5, 6, 7, 8, 10, 11, and 12, fasting blood samples are collected for measurement of serum cortisol at 4 hours (15 minutes) post-dose (~1200 hr). On Days in which the ACTH-stimulation test is conducted, this collection will be 120 min post-cosyntropin administration such that post-cosyntropin cortisol collection times are Time 30 minutes (5 minutes), Time 60 minutes (5 minutes), and Time 120 minutes (5 minutes).

24-Hour Biomarker:

A 24-hour blood biomarker profile is measured starting Day −1 until Day 1 pre-dose, Day 1 post-dose until Day 2 pre-dose, Day 4 post-dose until Day 5 pre-dose, and Day 9 post-dose until Day 10 pre-dose.

The first blood sample of the profile is collected as part of the 0800 hr morning (fasting) blood biomarker assessment, the remaining 5 samples are collected every 4 hours (±15 minutes) at e.g., 4 hours/1200 hr (fasting), 8 hours/1600 hr, 12 hours/2000 hr, 16 hours (fasting) 2400 hr (midnight), and 20 hours/0400 hr (fasting) post-dose. Serum cortisol, A4, 17 OHP, and ACTH(1-39) are measured at each timepoint.

Salivary Cortisol

For assessment of 24-hour salivary cortisol in the MAD, saliva samples are collected every 4 hours (±15 minutes) at e.g., 4 hours/1200 hr (fasting), 8 hours/1600 hr, 12 hours/ 2000 hr, 16 hours (fasting) 2400 hr (midnight), and 20 hours/0400 hr (fasting) post-dose starting at pre-dose.

Urine Free Cortisol (UFC)

For assessment of 24-hour UFC in the MAD, urine samples are collected for 24 hours in 3 pooled catches in 8 hour (±15 minutes) increments (i.e., 0 to 8 hours, 8 to 16 hours, 16 to 24 hours). The subject should void within 30 minutes prior to study drug dosing. Measure urine creatinine and urine volume output after each catch.

Results from the SAD Study

Figure 7:
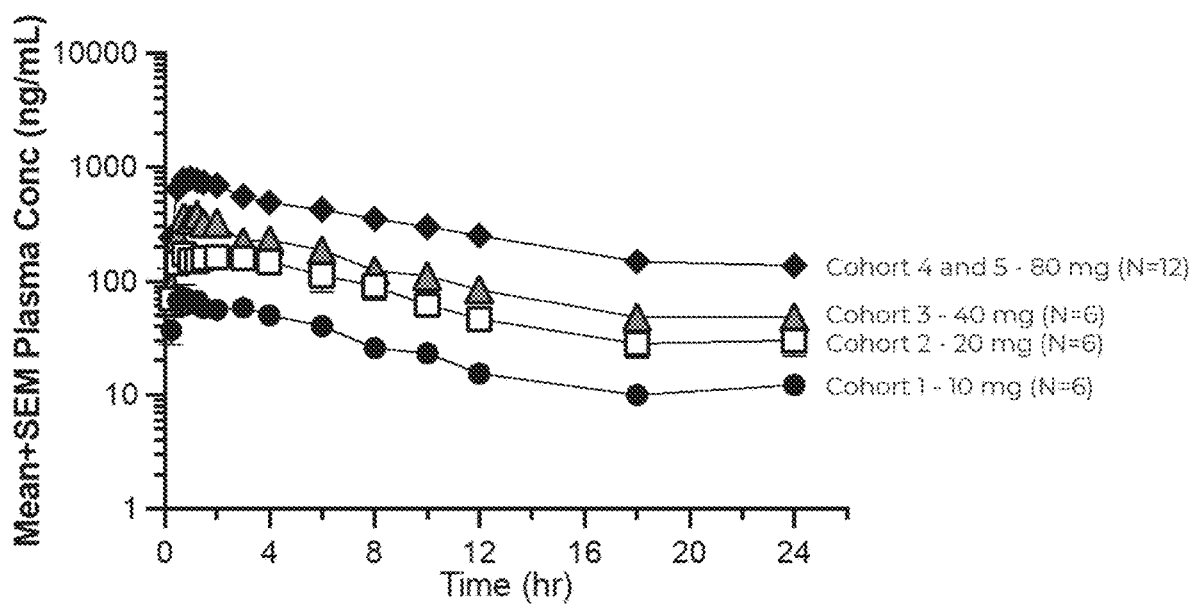
FIG. 7 shows the pharmacokinetic results from the single ascending dose (SAD) study of Compound 1.

Pharmacokinetic results from the SAD study are shown in FIG. 7. Data shown are mean±SEM. All doses n=6. Cohort 4 (n=6, 80 mg) was evaluated in the high dose ACTH-stimulation test, while cohort 5 (n=6, 80 mg) was evaluated in the low dose ACTH-stimulation test. A half-life ~24 hours was observed and tmax ~1 hr at efficacious doses.

Compound 1 showed oral bioavailability with dose-proportional exposure.

Compound 1 was also evaluated in the context of an ACTH-Stimulation Test, with oral Compound 1 or placebo being administered prior to the intravenous (IV) administration of cosyntropin (ACTH(1-24)). In the absence of pharmacologic intervention, IV administration of ACTH leads to the secretion of cortisol; whereas the pharmacologic intervention can suppress secretion of unstimulated basal cortisol levels.

Figure 8:
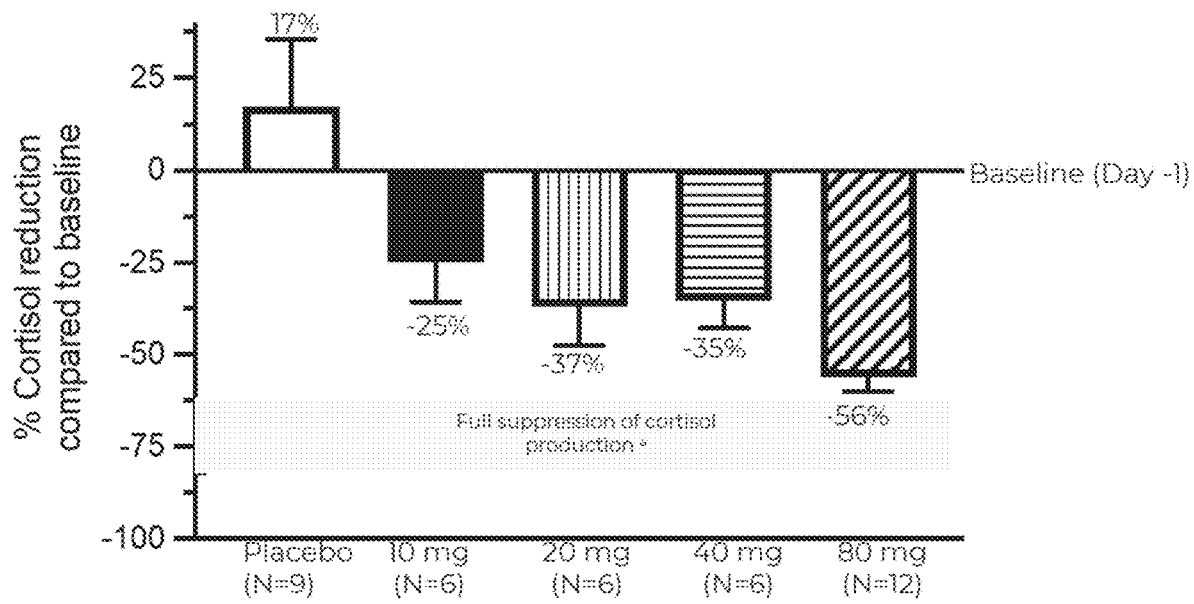
FIG. 8 shows the dose-dependent suppression of basal cortisol output from adrenal glands from the single ascending dose (SAD) study of Compound 1.

Oral administration of Compound 1 rapidly reduced basal cortisol output from adrenal glands. Acute reduction of basal cortisol (56% @ 80 mg) 2 hours after administration of Compound 1 was observed as shown in FIG. 8. Full suppression of cortisol production assumes no more cortisol is produced at time of Compound 1 dose and cortisol half-life is 66±18 minutes (see McKay Li, Cidlowski, J A. Pharmacokinetics of Corticosteroids in Kufe D W et al, editors, Holland-Frei Cancer Medicine 6$^{th}$ edition. Hamilton (ON) 2003). Data shown are mean±SEM.

Figure 9:
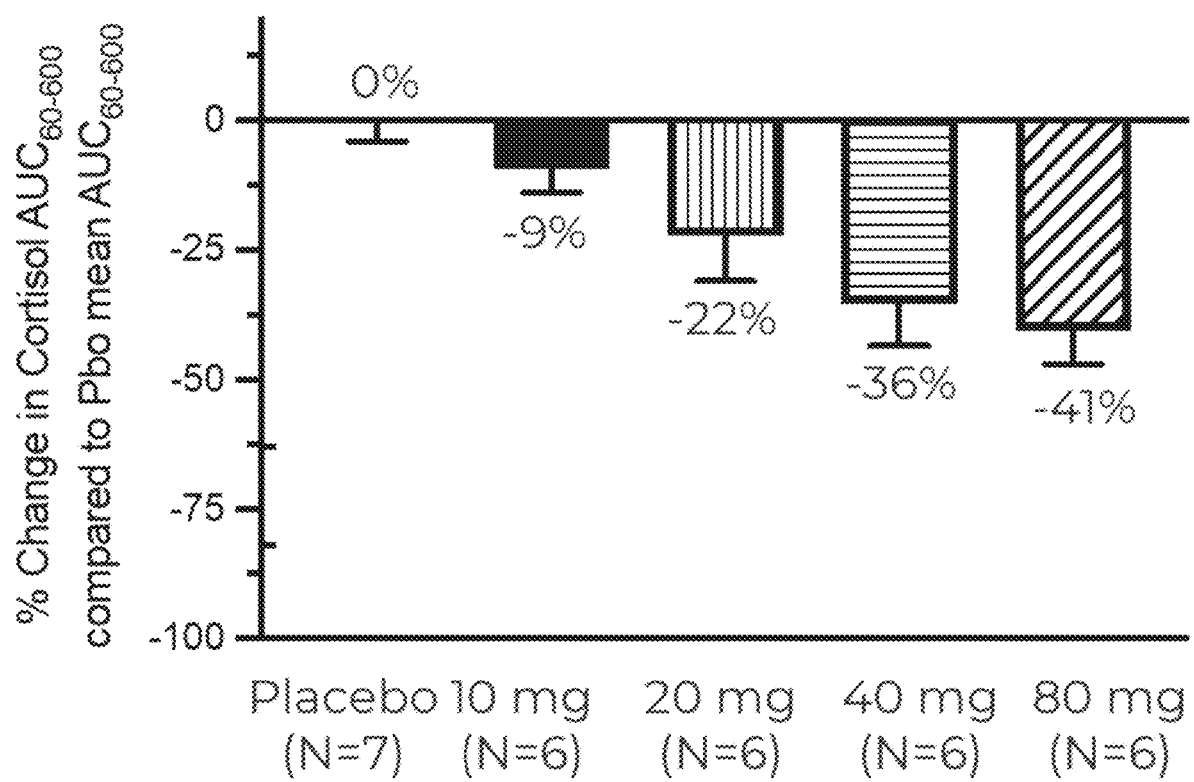
FIG. 9 shows the dose-dependent suppression of cortisol following supra-pathophysiological ACTH challenge from the single ascending dose (SAD) study of Compound 1.

Oral administration of Compound 1 prior to cosyntropin (ACTH(1-24)) showed a dose-dependent, strong cortisol suppression (41%) following supra-pathophysiologic high dose ACTH (250 mcg) challenge (FIG. 9). The measured % suppression in cortisol AUC was about 9%, about 22%, about 36%, and about 41%, respectively for the 10 mg, 20 mg, 40 mg, and 80 mg dose.

Figure 10:
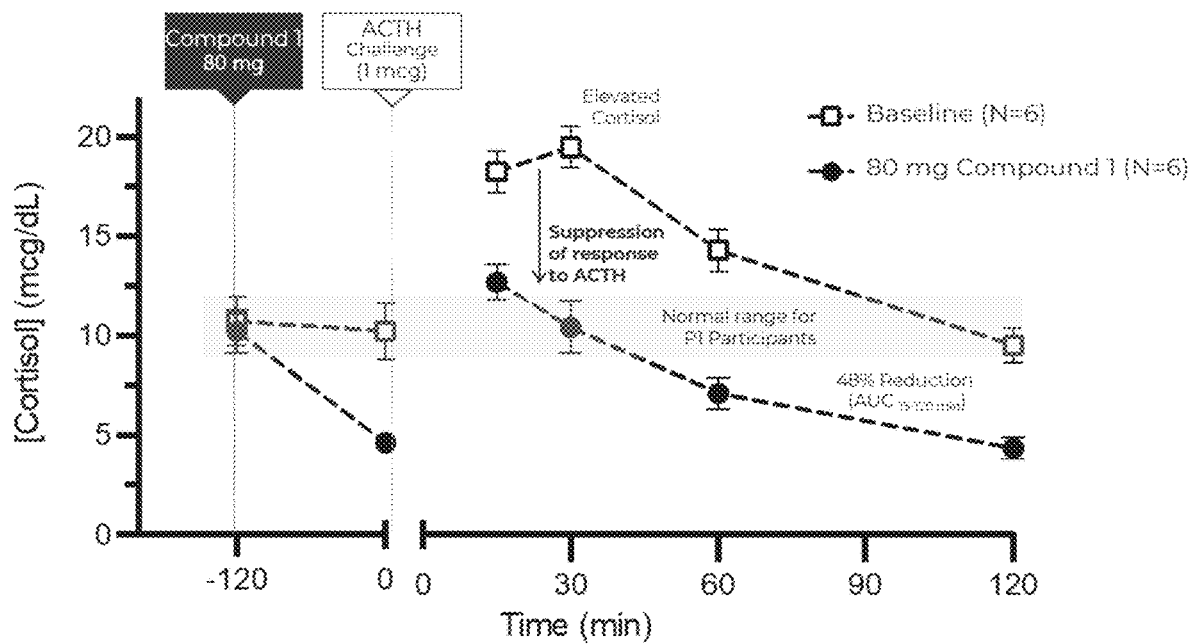
FIG. 10 shows the suppression of basal and ACTH-stimulated cortisol levels in the low dose (1 mcg) ACTH-stimulation test with treatment with Compound 1.
Figure 11:
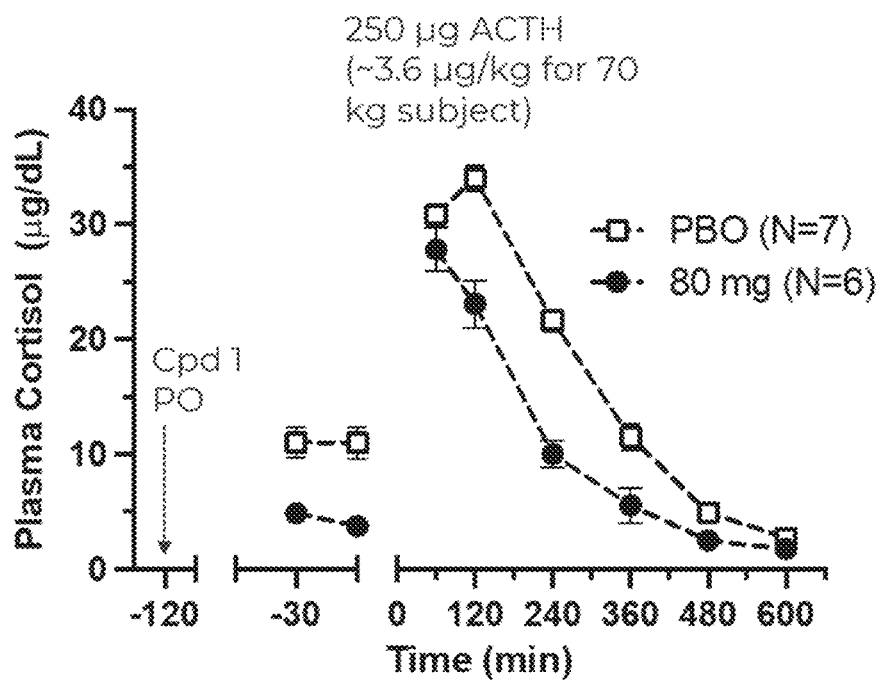
FIG. 11 shows the effect of 80 mg Compound 1 in the high dose (250 mcg) and low dose (1 mcg) ACTH-stimulation test.
Figure 11:
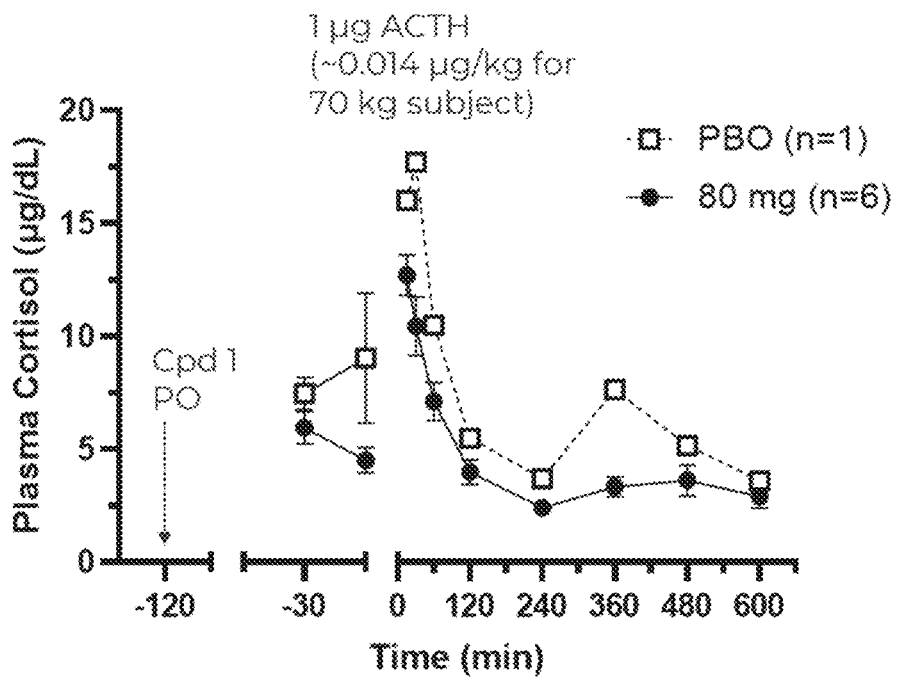

Oral administration of Compound 1 (80 mg) also demonstrated maintenance of normal cortisol levels in the more disease-relevant low dose ACTH (1 mcg) stimulation challenge, showing a 48% reduction in cortisol levels (FIG. 10). Cortisol secretion was suppressed in both the high dose (250 mcg) and low dose (1 mcg) cosyntropin challenge tests in subjects treated with 80 mg of Compound 1 (FIG. 11). PBO=placebo.

Results from the MAD Study

Figure 12:
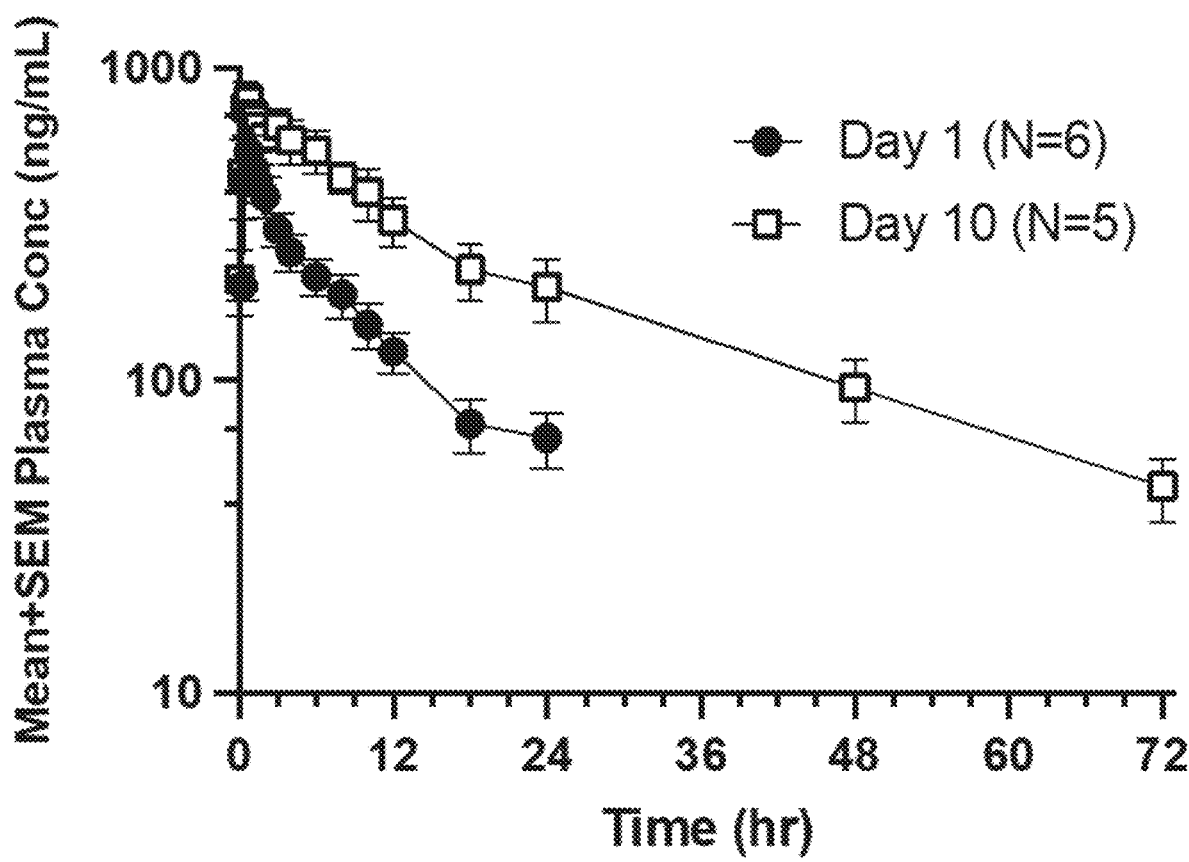
FIG. 12 shows the pharmacokinetic results for Day 1 and Day 10 after treatment with a 40 mg daily dose of Compound 1 over 10 days.

Pharmacokinetic results for Day 1 and Day 10 from the MAD study using a 40 mg daily dose of Compound 1 over 10 days are shown in FIG. 12. Data shown are mean±SEM. The Day 1 PK profile and exposures were comparable to the 40 mg single dose from the SAD study. The mean half-life was ~30 hours. Due to reduced clearance, accumulation with chronic dosing was approximately 2.4-fold higher than projected from SAD study results.

Figure 13:
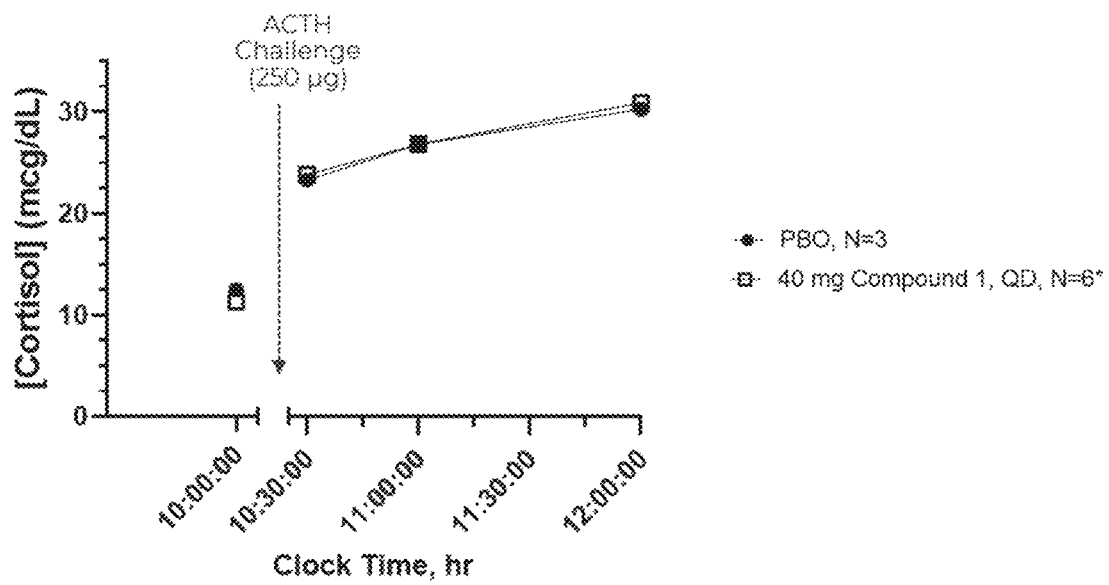
FIG. 13 shows the effect of Compound 1 on basal and ACTH-stimulated cortisol levels after 10 days of daily dosing of Compound 1.
Figure 13:
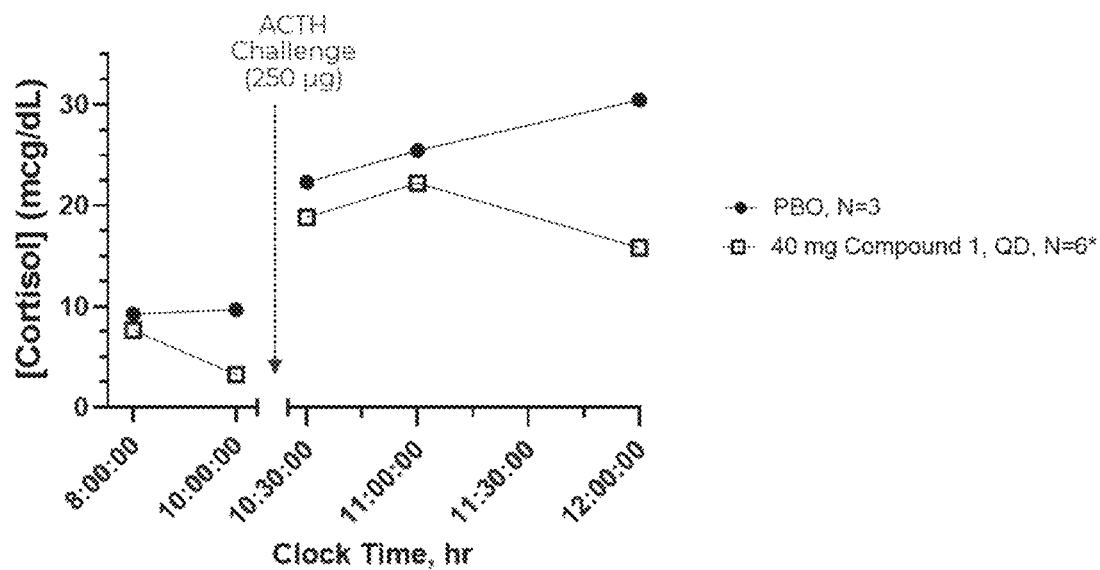
Figure 14:
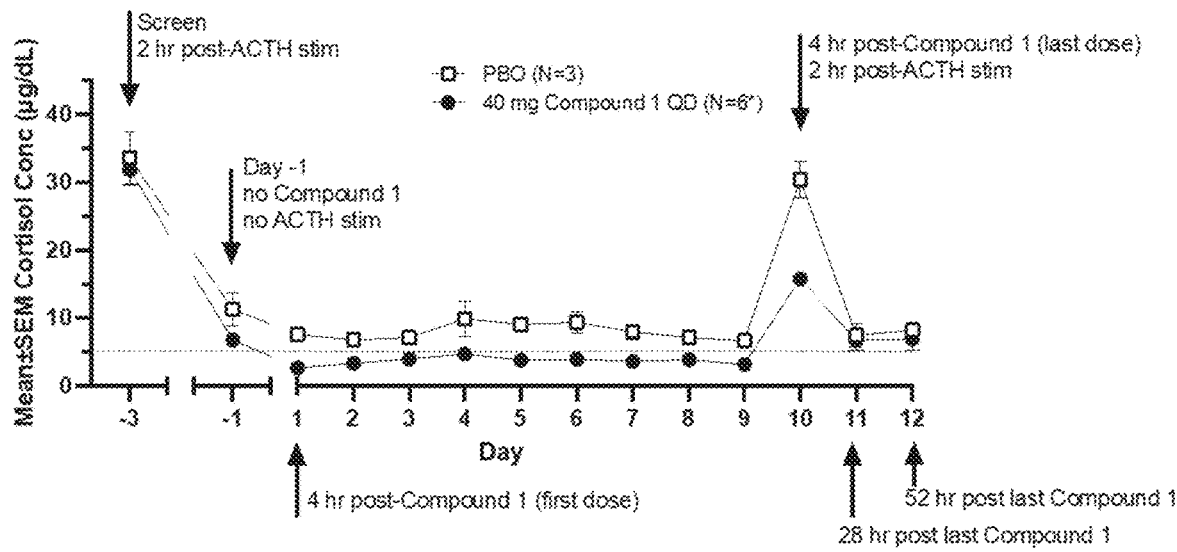
FIG. 14 shows the suppression of basal and ACTH-stimulated cortisol secretion at 4 h post-dose and 24 h post-dose throughout the 10-day study.
Figure 14:
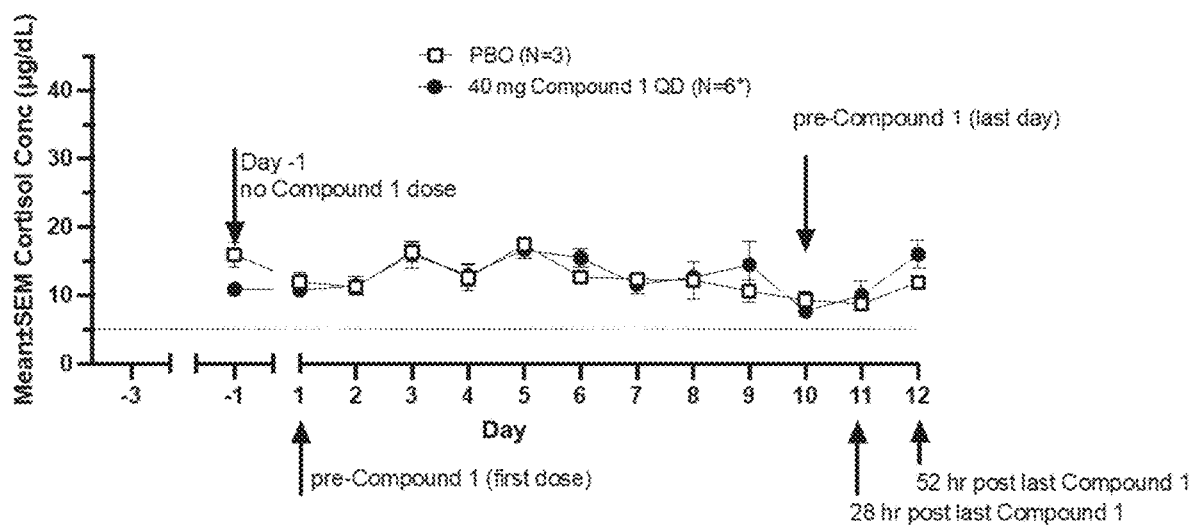
Figure 15:
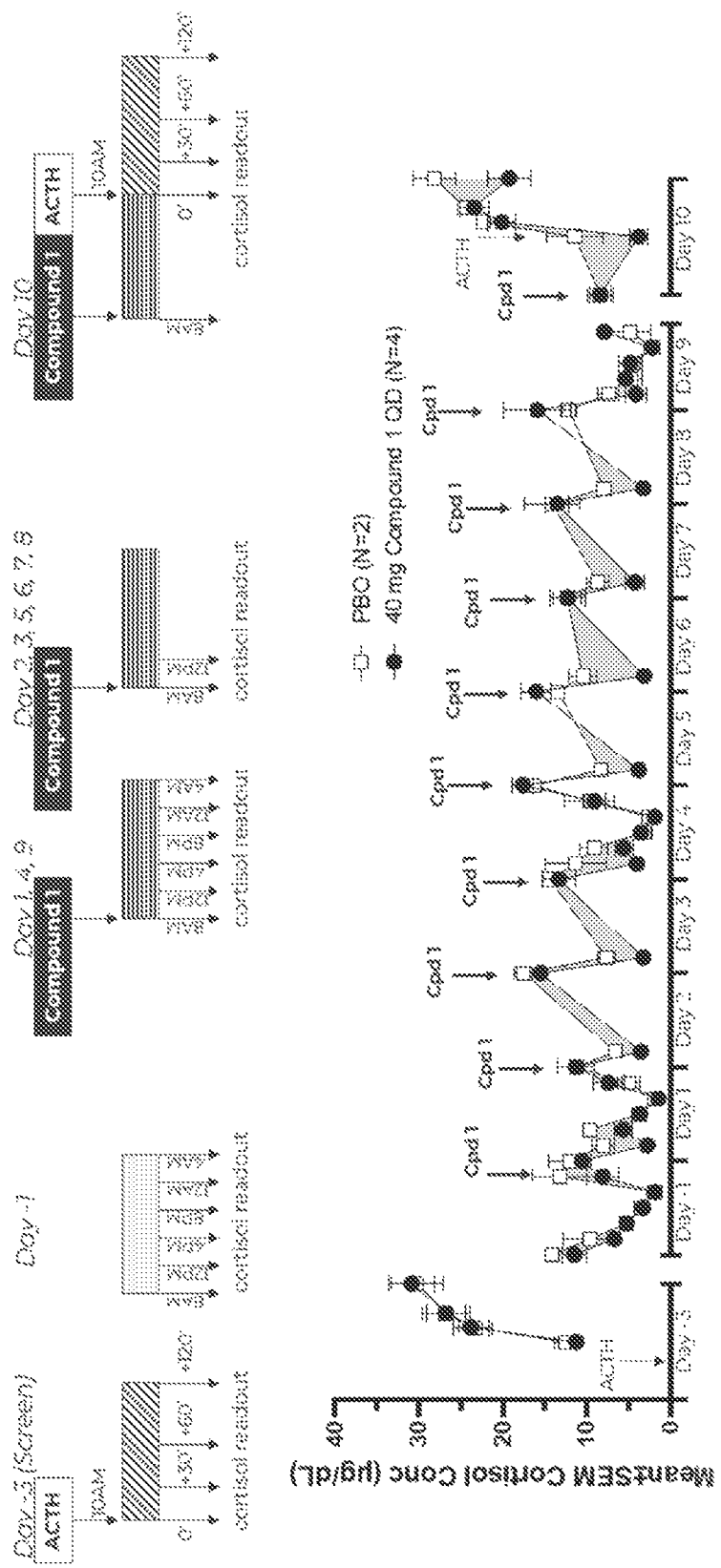
FIG. 15 shows the suppression of ACTH-stimulated cortisol throughout the 10 day study using 24-hour circadian sampling to monitor cortisol levels in serum.

In the high dose ACTH-stimulation test, Compound 1 suppressed basal and ACTH-stimulated cortisol levels after 10 days of dosing (FIG. 13). Compound 1 also suppressed basal and ACTH-stimulated cortisol secretion 4 h post-dose throughout the MAD study; however, suppression of basal unstimulated cortisol was not observed at 24 hours (before the next dose) (FIG. 14). Accordingly, maximum cortisol suppression occurs earlier in the diurnal cycle throughout the MAD study as observed by 24-hour circadian sampling (FIG. 15). PBO=placebo While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating Cushing's disease or ectopic ACTH syndrome (EAS) in a human, the method comprising administering to the human in need thereof a therapeutically effective amount of a compound having the structure of Compound 1, or a pharmaceutically acceptable salt thereof:

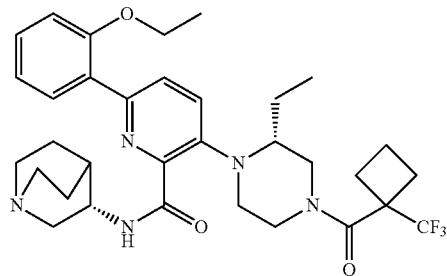

(Compound 1)

wherein treating Cushing's disease or EAS comprises reducing ACTH-stimulated cortisol levels in the human, and wherein ACTH-stimulated cortisol levels are reduced by at least about 35% in the human.

2. The method of claim 1, wherein the human produces excess ACTH.

3. The method of claim 2, wherein the human has a pituitary adenoma, a corticotroph adenoma, or an ectopic ACTH-secreting tumor.

4. The method of claim 1, wherein treating Cushing's disease or EAS comprises:
reducing levels of cortisol in the blood, serum, saliva, or urine of the human;
or reducing cortisol levels to the average level of a human without Cushing's disease or EAS, or a combination thereof;
or reducing growth of fat pads (collarbone, back of neck, face and trunk), excessive sweating, dilation of capillaries, thinning of the skin, muscle weakness, hirsutism, depression/anxiety, hypertension, osteoporosis, insulin resistance, hyperglycemia, heart disease, lethargy, obesity, menstrual irregularity, or combinations thereof; or a combination thereof.

5. The method of claim 2, wherein the human with Cushing's disease or ectopic ACTH syndrome (EAS) has a non-pituitary tumor that secretes excessive amounts of ACTH, wherein the non-pituitary tumor is in the lungs, pancreas, thyroid, thymus gland, intestines, adrenal gland, or paraganglia.

6. A method of reducing levels of ACTH-stimulated cortisol in a human, the method comprising administering to the human in need thereof a therapeutically effective amount of a compound having the structure of Compound 1, or a pharmaceutically acceptable salt thereof:

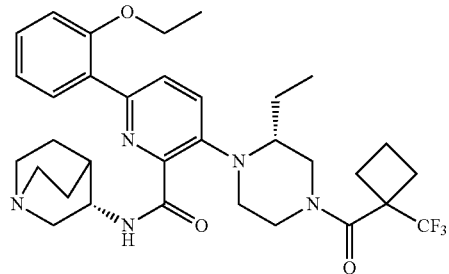

(Compound 1)

wherein the human has Cushing's disease or ectopic ACTH syndrome (EAS); and
wherein reducing the levels of ACTH-stimulated cortisol reduces or alleviates one or more symptoms of Cushing's disease or EAS in the human; and wherein ACTH-stimulated cortisol levels in the human are reduced by at least about 35%.

7. The method of claim 1, wherein Compound 1, or a pharmaceutically acceptable salt thereof, is administered orally in amount equivalent to about 40 mg of Compound 1.

8. The method of claim 1, wherein Compound 1, or a pharmaceutically acceptable salt thereof, is administered orally in amount equivalent to about 80 mg of Compound 1.

9. The method of claim 1, wherein Compound 1, or a pharmaceutically acceptable salt thereof, is administered orally in amount equivalent to about 120 mg of Compound 1.

10. The method of claim 1, wherein Compound 1, or a pharmaceutically acceptable salt thereof, is administered orally in amount equivalent to about 160 mg of Compound 1.

11. The method of claim 6, wherein Compound 1, or a pharmaceutically acceptable salt thereof, is administered orally in amount equivalent to about 40 mg of Compound 1.

12. The method of claim 6, wherein Compound 1, or a pharmaceutically acceptable salt thereof, is administered orally in amount equivalent to about 80 mg of Compound 1.

13. The method of claim 6, wherein Compound 1, or a pharmaceutically acceptable salt thereof, is administered orally in amount equivalent to about 120 mg of Compound 1.

14. The method of claim 6, wherein Compound 1, or a pharmaceutically acceptable salt thereof, is administered orally in amount equivalent to about 160 mg of Compound 1.

15. The method of claim 1, wherein ACTH-stimulated cortisol levels are reduced by at least about 40% in the human.

16. The method of claim 1, wherein ACTH-stimulated cortisol levels are reduced by at least about 45% in the human.

17. The method of claim 6, wherein ACTH-stimulated cortisol levels are reduced by at least about 40% in the human.

18. The method of claim 6, wherein ACTH-stimulated cortisol levels are reduced by at least about 45% in the human.

* * * * *

UNITED STATES PATENT AND TRADEMARK OFFICE
CERTIFICATE OF CORRECTION

| | | |
|---|---|---|
| PATENT NO. | : 12,280,046 B2 | Page 1 of 1 |
| APPLICATION NO. | : 17/696279 | |
| DATED | : April 22, 2025 | |
| INVENTOR(S) | : Ferrara et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 103 days.

Signed and Sealed this
Sixth Day of January, 2026

John A. Squires
*Director of the United States Patent and Trademark Office*